(12) United States Patent
Kuwabara

(10) Patent No.: US 11,185,303 B2
(45) Date of Patent: Nov. 30, 2021

(54) IMAGE PROCESSING APPARATUS, RADIOGRAPHY SYSTEM, IMAGE PROCESSING METHOD, AND IMAGE PROCESSING PROGRAM

(71) Applicant: FUJIFILM Corporation, Tokyo (JP)

(72) Inventor: Takeshi Kuwabara, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 95 days.

(21) Appl. No.: 16/378,003

(22) Filed: Apr. 8, 2019

(65) Prior Publication Data

US 2019/0313994 A1 Oct. 17, 2019

(30) Foreign Application Priority Data

Apr. 11, 2018 (JP) .............................. JP2018-076441

(51) Int. Cl.
*A61B 6/00* (2006.01)
*G01T 1/20* (2006.01)
*G01T 1/202* (2006.01)

(52) U.S. Cl.
CPC .......... *A61B 6/5282* (2013.01); *A61B 6/4233* (2013.01); *A61B 6/4266* (2013.01); *A61B 6/482* (2013.01); *A61B 6/505* (2013.01); *G01T 1/2006* (2013.01); *G01T 1/2023* (2013.01)

(58) Field of Classification Search
CPC ... A61B 6/5282; A61B 6/4233; A61B 6/4266; A61B 6/482; A61B 6/505; A61B 6/4241; G01T 1/2006; G01T 1/2023
See application file for complete search history.

(56) References Cited

U.S. PATENT DOCUMENTS

2003/0026385 A1 2/2003 Dinten et al.
2006/0008046 A1* 1/2006 Ruhrnschopf ....... G01N 23/046
378/7

(Continued)

FOREIGN PATENT DOCUMENTS

JP 2-244881 A 9/1990
JP 4-11473 A 1/1992

(Continued)

OTHER PUBLICATIONS

Extended European Search Report, dated Aug. 8, 2019, for European Application No. 19167750.9.

(Continued)

*Primary Examiner* — Christine S. Kim
(74) *Attorney, Agent, or Firm* — Birch, Stewart, Kolasch & Birch, LLP.

(57) ABSTRACT

An image processing apparatus includes: an acquisition unit that acquires a radiographic image generated by a radiation detector irradiated with radiation from a radiography apparatus including the radiation detector in which plural pixels, each of which includes a conversion element that generates a larger amount of charge as it is irradiated with a larger amount of radiation, are arranged; and a correction unit that corrects scattered ray components caused by scattered rays of the radiation included in the radiographic image on the basis of region information indicating a region of the radiation detector irradiated with radiation transmitted through a subject, using scattered ray correction data.

11 Claims, 14 Drawing Sheets

(56) References Cited

U.S. PATENT DOCUMENTS

| | | | |
|---|---|---|---|
| 2009/0103679 A1* | 4/2009 | Jabri | A61B 6/488 378/70 |
| 2009/0232272 A1 | 9/2009 | Tsujii et al. | |
| 2017/0238887 A1* | 8/2017 | Karim | G01T 1/2018 |
| 2017/0262976 A1 | 9/2017 | Choi et al. | |
| 2018/0020999 A1* | 1/2018 | Yamamoto | A61B 6/025 378/4 |
| 2018/0028139 A1 | 2/2018 | Kuwabara | |
| 2018/0364373 A1* | 12/2018 | Hondongwa | G01T 1/17 |

FOREIGN PATENT DOCUMENTS

| | | |
|---|---|---|
| JP | 2003-515376 A | 5/2003 |
| JP | 2015-208638 A | 11/2015 |
| JP | 2016-131805 A | 7/2016 |
| JP | 2018-015453 A | 2/2018 |

OTHER PUBLICATIONS

Japanese Office Action, dated Jun. 1, 2021, for Japanese Application No. 2018-076441 with English Translation.

* cited by examiner

IMAGE PROCESSING APPARATUS, RADIOGRAPHY SYSTEM, IMAGE PROCESSING METHOD, AND IMAGE PROCESSING PROGRAM

CROSS-REFERENCE TO RELATED APPLICATION

This application claims priority from Japanese Patent Application No. 2018-076441, filed on Apr. 11, 2018, the disclosure of which is incorporated by reference herein in its entirety.

BACKGROUND

Field of the Invention

The present disclosure relates to an image processing apparatus, a radiography system, an image processing method, and a storage medium storing an image processing program.

Related Art

A technique has been disclosed which subtracts a scattered ray image generated by a scattering function from a radiographic image generated by a radiation detector to reduce scattered ray components included in the radiographic image (see JP2015-208638A).

However, in recent years, it is desirable to stably and accurately correct components caused by the scattered rays of radiation included in a radiographic image. For example, in a method for calculating a numerical value from a radiographic image, such as a dual-energy X-ray absorptiometry (DXA) method for deriving the bone density of a subject from a radiographic image, it is desirable to stably correct components caused by the scattered rays of radiation included in a radiographic image with higher accuracy.

However, in the technique disclosed in JP2015-208638A, a difference in energy between two radiographic images obtained by irradiation with radiations having different energy levels used in, for example, the DXA method is not considered. Therefore, in some cases, it is difficult to correct components caused by the scattered rays of radiation included in a radiographic image with high accuracy.

SUMMARY

The present disclosure has been made in view of the above-mentioned problems and an object of the present disclosure is to provide an image processing apparatus, a radiography system, an image processing method, and a storage medium storing an image processing program that can correct components caused by the scattered rays of radiation included in a radiographic image with high accuracy.

In order to achieve the object, according to a first aspect of the present disclosure, there is provided an image processing apparatus comprising: an acquisition unit that acquires a radiographic image generated by a radiation detector irradiated with radiation from a radiography apparatus including the radiation detector in which a plurality of pixels, each of which includes a conversion element that generates a larger amount of charge as it is irradiated with a larger amount of radiation, are arranged; and a correction unit that corrects scattered ray components caused by scattered rays of the radiation included in the radiographic image on the basis of region information indicating a region of the radiation detector irradiated with radiation transmitted through a subject, using scattered ray correction data.

According to a second aspect of the present disclosure, in the image processing apparatus according to the first aspect, the correction unit may correct the scattered ray components, using scattered ray correction data corrected on the basis of the region information.

According to a third aspect of the present disclosure, in the image processing apparatus according to the first or second aspect, the region information may be image information obtained by binarizing a pixel value of the radiographic image.

According to a fourth aspect of the present disclosure, in the image processing apparatus according to any one of the first to third aspects, the scattered ray correction data may include information indicating intensity of the scattered rays and information indicating a spread of the scattered rays.

According to a fifth aspect of the present disclosure, in the image processing apparatus according to any one of the first to fourth aspects, the radiography apparatus may include two radiation detectors, that is, a first radiation detector and a second radiation detector. The first radiation detector and the second radiation detector may be arranged in a direction in which the radiation is emitted. The acquisition unit may acquire a first radiographic image generated by the first radiation detector irradiated with radiation with a first energy level and a second radiographic image generated by the second radiation detector irradiated with radiation with a second energy level different from the first energy level. The correction unit may correct the scattered ray components included in the first radiographic image, using first correction data for correcting the scattered rays which is associated with the region information and the first radiation detector, and correct the scattered ray components included in the second radiographic image, using second correction data for correcting the scattered rays which is associated with the region information and the second radiation detector and is different from the first correction data for correcting the scattered rays.

According to a sixth aspect of the present disclosure, in the image processing apparatus according to any one of the first to fourth aspects, the acquisition unit may acquire a first radiographic image generated by the radiation detector irradiated with radiation with a first energy level and a second radiographic image generated by the radiation detector irradiated with radiation with a second energy level different from the first energy level. The correction unit may correct the scattered ray components included in the first radiographic image, using first correction data for correcting the scattered rays which is associated with the region information and the first energy level, and correct the scattered ray components included in the second radiographic image, using second correction data for correcting the scattered rays which is associated with the region information and the second energy level and is different from the first correction data for correcting the scattered rays.

According to a seventh aspect of the present disclosure, the image processing apparatus according to the fifth or sixth aspect may further comprise a derivation unit that derives at least one of bone density or bone mineral content, using the first radiographic image and the second radiographic image corrected by the correction unit.

According to an eighth aspect of the present disclosure, in the image processing apparatus according to the fifth aspect, each of the first and second radiation detectors may comprise a light emitting layer that is irradiated with the radiation and emits light. The plurality of pixels of each of the first and second radiation detectors may receive the light, generate charge, and accumulate the charge. The light emitting layer of one of the first and second radiation detectors which is provided on an incident side of the radiation may include CsI and the light emitting layer of the other radiation detector may include GOS.

According to a ninth aspect of the present disclosure, there is provided a radiography system comprising: the image processing apparatus according to any one of the first to eighth aspects; and a radiography apparatus that outputs a radiographic image to the image processing apparatus.

According to a tenth aspect of the present disclosure, there is provided an image processing method comprising: acquiring a radiographic image generated by a radiation detector irradiated with radiation from a radiography apparatus including the radiation detector in which a plurality of pixels, each of which includes a conversion element that generates a larger amount of charge as it is irradiated with a larger amount of radiation, are arranged; and correcting scattered ray components caused by scattered rays of the radiation included in the radiographic image on the basis of region information indicating a region of the radiation detector irradiated with radiation transmitted through a subject, using scattered ray correction data.

According to an eleventh aspect of the present disclosure, there is provided a non-transitory storage medium storing a program that causes a computer to perform an image processing, the image processing including: acquiring a radiographic image generated by a radiation detector irradiated with radiation from a radiography apparatus including the radiation detector in which a plurality of pixels, each of which includes a conversion element that generates a larger amount of charge as it is irradiated with a larger amount of radiation, are arranged; and correcting scattered ray components caused by scattered rays of the radiation included in the radiographic image on the basis of region information indicating a region of the radiation detector irradiated with radiation transmitted through a subject, using scattered ray correction data.

According to the present disclosure, it is possible to correct components caused by scattered rays of radiation included in a radiographic image with high accuracy.

DETAILED DESCRIPTION

Hereinafter, embodiments of the present disclosure will be described in detail with reference to the drawings.

First Embodiment

Figure 1:
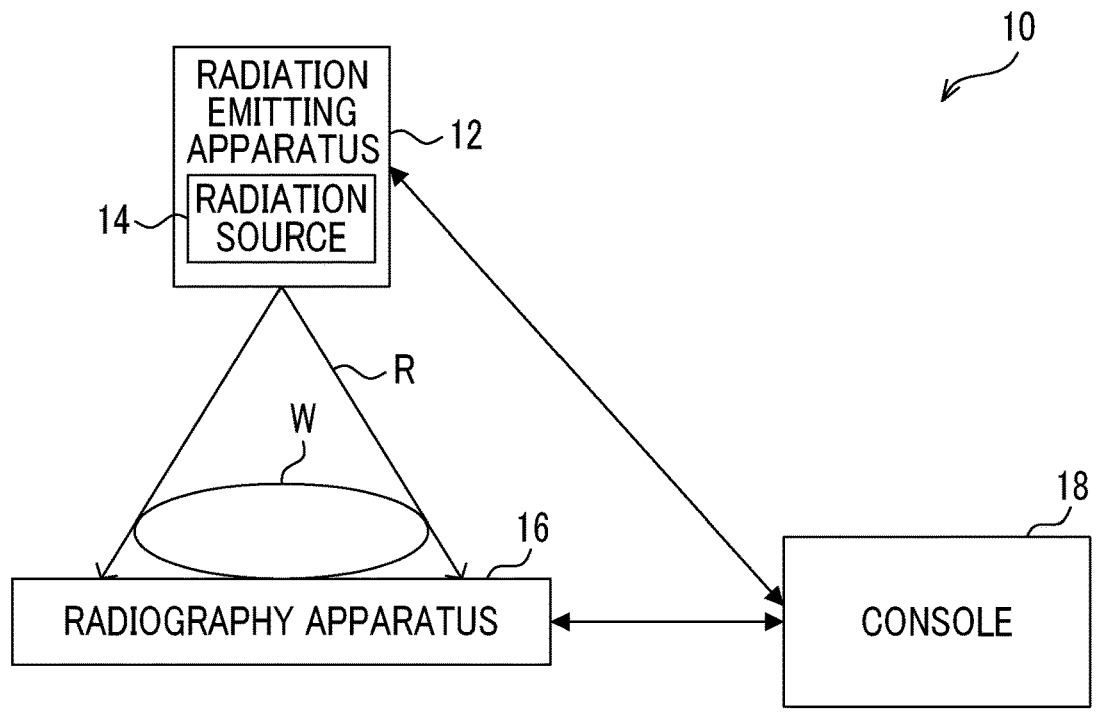
FIG. 1 is a block diagram illustrating an example of the configuration of a radiography system according to each embodiment.

First, the configuration of a radiography system 10 according to this embodiment will be described with reference to FIG. 1. As illustrated in FIG. 1, the radiography system 10 includes a radiation emitting apparatus 12, a radiography apparatus 16, and a console 18. The console 18 is an example of an image processing apparatus according to the present disclosure.

The radiation emitting apparatus 12 according to this embodiment includes a radiation source 14 that irradiates a subject W, which is an example of an imaging target, with radiation R such as X-rays. The radiation emitting apparatus 12 according to this embodiment emits the radiation R with a cone-beam shape. An example of the radiation emitting apparatus 12 is a treatment cart. A method for commanding the radiation emitting apparatus 12 to emit the radiation R is not particularly limited. For example, in a case in which the radiation emitting apparatus 12 includes an irradiation button, a user, such as a radiology technician, may press the irradiation button to command the emission of the radiation R such that the radiation R is emitted from the radiation emitting apparatus 12. In addition, for example, the user, such as a radiology technician, may operate the console 18 to command the emission of the radiation R such that the radiation R is emitted from the radiation emitting apparatus 12.

In a case in which the command to emit the radiation R is received, the radiation emitting apparatus 12 emits the radiation R from the radiation source 14 according to set emission conditions, such as a tube voltage, a tube current, and an emission period. Hereinafter, the dose of the radiation R is simply referred to as "the amount of radiation".

Figure 2:
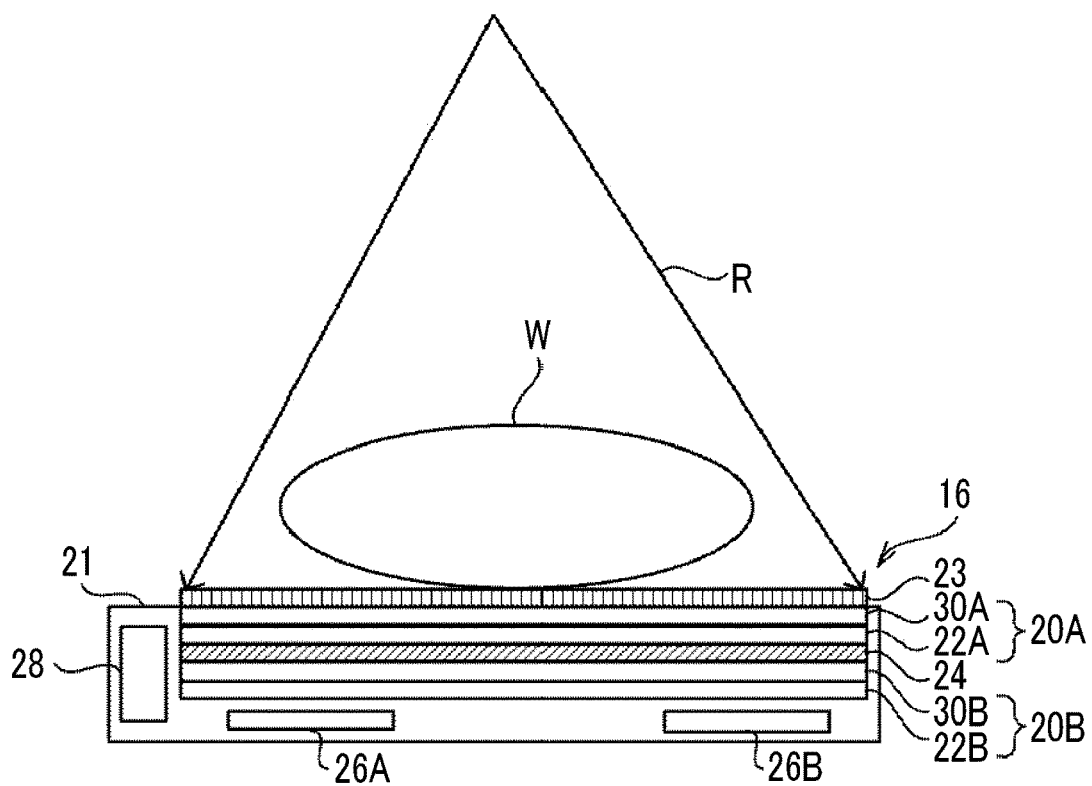
FIG. 2 is a side cross-sectional view illustrating an example of the configuration of a radiography apparatus according to a first embodiment.

Next, the configuration of the radiography apparatus 16 according to this embodiment will be described with reference to FIG. 2. As illustrated in FIG. 2, the radiography apparatus 16 includes a plate-shaped housing 21 that transmits the radiation R and has a waterproof, antibacterial, and airtight structure. The housing 21 includes a first radiation detector 20A and a second radiation detector 20B that detect the radiation R transmitted through the subject W. In addition, the housing 21 includes a radiation limitation member 24, a control substrate 26A, a control substrate 26B, and a case 28. The radiography apparatus 16 captures radiographic images of the subject W using the first radiation detector 20A and the second radiation detector 20B. Hereinafter, in a case in which the first radiation detector 20A and the second radiation detector 20B do not need to be distinguished from each other, they are generically referred to as "radiation detectors 20". In addition, a grid 23 for removing scattered rays is provided between the housing 21 and the subject W.

The first radiation detector 20A is provided on the incident side of the radiation R and the second radiation detector 20B is provided so as to be stacked on the side of the first radiation detector 20A from which the radiation R is transmitted and emitted. The first radiation detector 20A includes a thin film transistor (TFT) substrate 30A and a scintillator 22A which is an example of a light emitting layer that is irradiated with the radiation R and emits light. The TFT substrate 30A and the scintillator 22A are stacked in the order of the TFT substrate 30A and the scintillator 22A from the incident side of the radiation R. The term "stacked" means a state in which the first radiation detector 20A and the second radiation detector 20B overlap each other in a case in which the first radiation detector 20A and the second radiation detector 20B are seen from the incident side or the emission side of the radiation R in the radiography apparatus 16 and it does not matter how they overlap each other. For example, the first radiation detector 20A and the second radiation detector 20B, or the first radiation detector 20A, the radiation limitation member 24, and the second radiation detector 20B may overlap while coming into contact with each other or may overlap with a gap therebetween in the stacking direction.

The second radiation detector 20B includes a TFT substrate 30B and a scintillator 22B which is an example of the light emitting layer. The TFT substrate 30B and the scintillator 22B are stacked in the order of the TFT substrate 30B and the scintillator 22B from the incident side of the radiation R.

That is, the first radiation detector 20A and the second radiation detector 20B are irradiation side sampling (ISS) radiation detectors that are irradiated with the radiation R from the side of the TFT substrates 30A and 30B.

In the radiography apparatus 16 according to this embodiment, the scintillator 22A of the first radiation detector 20A and the scintillator 22B of the second radiation detector 20B have different compositions. Specifically, for example, the scintillator 22A includes CsI (Tl) (cesium iodide having thallium added thereto) and the scintillator 22B includes gadolinium oxysulfide (GOS). In addition, a combination of the composition of the scintillator 22A and the composition of the scintillator 22B is not limited to the above-mentioned example and may be a combination of other compositions or a combination of the same compositions.

For example, the scintillators 22A and 22B have emission characteristics that vary depending on a thickness. As the thickness increases, the amount of light emitted increases and sensitivity increases. However, image quality deteriorates due to, for example, light scattering.

For example, in a case in which the scintillators 22A and 22B are formed by being filled with particles which are irradiated with the radiation R and emit light, such as GOS particles, as the diameter of the particle increases, the amount of light emitted increases and sensitivity increases. However, the amount of light scattering increases and the increase in the amount of light scattering affects adjacent pixels 32 (see FIG. 3), which results in the deterioration of image quality.

In addition, the scintillators 22A and 22B may have a multi-layered structure of a small-particle layer and a large-particle layer. For example, in a case in which each of the first radiation detector 20A and the second radiation detector 20B is irradiated with the radiation R from the scintillators 22A and 22B to the TFT substrates 30A and 30B unlike the radiography apparatus 16 according to this embodiment, the following occurs. That is, in this case, image blurring is small in the scintillators 22A and 22B in which a region close to the irradiation side of the radiation R is filled with small particles and a region close to the side of the TFT substrate 30 that is the emission side of the radiation R is filled with large particles. However, oblique components of light that is radially emitted by the small particles are less likely to reach the TFT substrates 30A and 30B and sensitivity is reduced. In addition, in a case in which the ratio of the region filled with small particles to the region filled with large particles is changed such that the number of layers formed by the region filled with large particles is larger than the number of layers formed by the region filled with small particles, sensitivity increases. However, in this case, light scattering affects adjacent pixels 32, which results in the deterioration of image quality.

As the filling rate of the particles increases, the sensitivity of the scintillators 22A and 22B increases. However, the amount of light scattering increases and image quality deteriorates. Here, the filling rate is a value obtained by dividing the total volume of the particles of the scintillator 22A or 22B by the volume of the scintillator 22A or 22B and multiplying the divided value by 100 (the total volume of the particles of the scintillator 22A or 22B/the volume of the scintillator 22A or 22B×100). In addition, powder is treated in the scintillators 22A and 22B. Therefore, in a case in which the filling rate is greater than 80 vol %, it is difficult to manufacture the scintillators 22A and 22B. For this reason, it is preferable that the filling rate is in the range of 50 vol % to 80 vol %.

In addition, the emission characteristics of the scintillators 22A and 22B vary depending on the doping amount of activator. As the doping amount of activator increases, the amount of light emitted tends to increase. However, the amount of light scattering increases and image quality deteriorates.

The emission characteristics of the scintillators 22A and 22B with respect to the radiation R vary depending on the material used for the scintillators 22A and 22B. For example, in a case in which each of the first radiation detector 20A and the second radiation detector 20B is irradiated with the radiation R from the scintillators 22A and 22B to the TFT substrates 30A and 30B unlike the radiography apparatus 16 according to this embodiment, the scintillator 22A is made of CsI (Tl) and the scintillator 22B is made of GOS. In this case, in the scintillator 22A, emphasis is put on image quality and the absorptivity of the low-energy radiation R is relatively high. In the scintillator 22B, the absorptivity of the high-energy radiation R is relatively high.

In addition, the scintillator 22A has a columnar separated layer structure, which makes it possible to further improve image quality.

In a case in which reflecting layers (not illustrated) that transmit the radiation R and reflect visible light are formed on the surfaces of the scintillators 22A and 22B which are opposite to the TFT substrates 30A and 30B, light generated by the scintillators 22A and 22B is more effectively guided to the TFT substrates 30A and 30B and sensitivity is improved. A method for forming the reflecting layer is not particularly limited. For example, any one of a sputtering method, a vapor deposition method, or a coating method may be used. It is preferable that the reflecting layer is made of a material with high reflectance in an emission wavelength range of the scintillators 22A and 22B used. For example, the reflecting layer is made of Au, Ag, Cu, Al, Ni, and Ti. For example, in a case in which the scintillators 22A and 22B are made of GOS:Tb, the reflecting layer is preferably made of Ag, Al, and Cu that have high reflectance in a wavelength of 400 nm to 600 nm. In a case in which the thickness of the reflecting layer is less than 0.01 μm, reflectance is not obtained. Even in a case in which the thickness is greater than 3 μm, the effect of further improving the reflectance is not obtained. For this reason, it is preferable that the thickness of the reflecting layer is in the range of 0.01 μm to 3 μm.

Therefore, the characteristics of the scintillators 22A and 22B may vary depending on the diameter of particles, the multi-layered structure of particles, the filling rate of particles, the doping amount of activator, a material, a change in layer structure, and the shape of the reflecting layer.

In addition, the grid 23 that removes scattered rays generated by the transmission of the radiation R through the subject W from the radiation R transmitted through the subject W is provided on the side of the first radiation detector 20A on which the radiation R is incident side. For example, the effect of suppressing a reduction in the contrast of a radiographic image is obtained by the removal of the scattered rays from the radiation R and the quality of the radiographic image is improved.

The radiation limitation member 24 that limits the transmission of the radiation R is provided between the first radiation detector 20A and the second radiation detector 20B. An example of the radiation limitation member 24 is a plate-shaped member made of, for example, copper or tin. It is preferable that the thickness of the plate-shaped member is uniform in the range in which an error of a variation in the thickness is equal to or less than 1%. In a case in which the first radiation detector 20A sufficiently absorbs the radiation R, the radiation limitation member 24 may not be provided.

The control substrate 26A is provided so as to correspond to the first radiation detector 20A and electronic circuits, such as an image memory 56A and a control unit 58A which will be described below, are formed on the control substrate 26A. The control substrate 26B is provided so as to correspond to the second radiation detector 20B and electronic circuits, such as an image memory 56B and a control unit 58B which will be described below, are formed on the control substrate 26B. The control substrate 26A and the control substrate 26B are provided on the side of the second radiation detector 20B which is opposite to the incident side of the radiation R.

The case 28 is provided at a position (that is, outside the range of an imaging region) that does not overlap the radiation detector 20 at one end of the housing 21. For example, a power supply unit 70 which will be described below is accommodated in the case 28. The installation position of the case 28 is not particularly limited. For example, the case 28 may be provided at a position that overlaps the radiation detector 20 on the side of the second radiation detector 20B which is opposite to the incident side of the radiation.

Next, the configuration of a main portion of an electric system of the radiography apparatus 16 according to this embodiment will be described with reference to FIG. 3.

Figure 3:
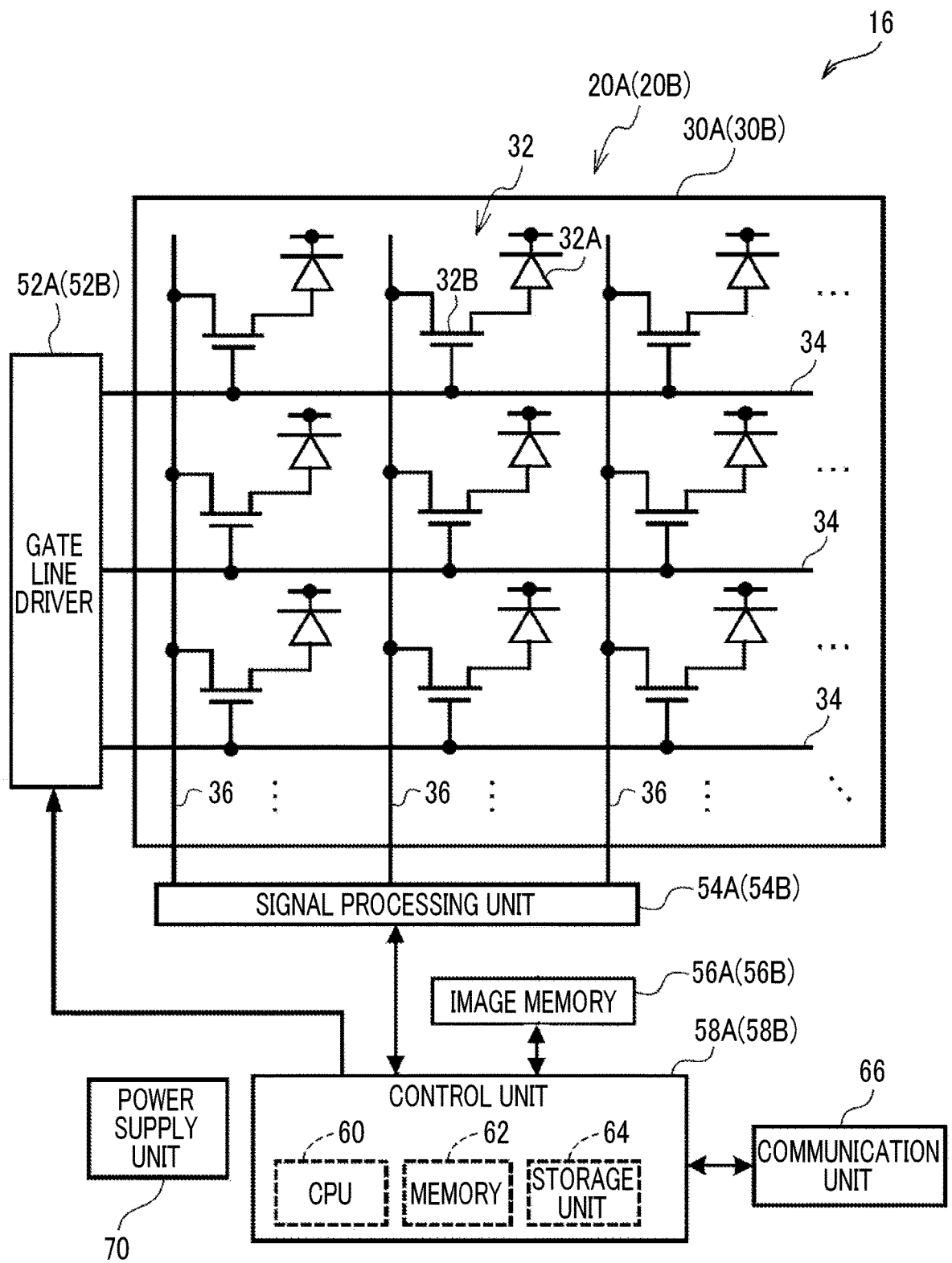
FIG. 3 is a block diagram illustrating an example of the configuration of a main portion of an electric system of a radiography apparatus according to each embodiment.

As illustrated in FIG. 3, a plurality of pixels 32 are two-dimensionally provided in one direction (a row direction in FIG. 3) and a cross direction (a column direction in FIG. 3) that intersects the one direction on the TFT substrate 30A. The pixel 32 includes a sensor unit 32A and a field effect thin film transistor (TFT; hereinafter, simply referred to as a "thin film transistor") 32B.

The sensor unit 32A includes, for example, an upper electrode, a lower electrode, and a photoelectric conversion film which are not illustrated, absorbs the light emitted from the scintillator 22A, generates charge, and accumulates the generated charge. The thin film transistor 32B converts the charge accumulated in the sensor unit 32A into an electric signal and outputs the electric signal. The sensor unit 32A is an example of a conversion element that generates a larger amount of charge as the amount of radiation becomes larger.

A plurality of gate lines 34 which extend in the one direction and are used to turn each thin film transistor 32B on and off are provided on the TFT substrate 30A. In addition, a plurality of data lines 36 which extend in the cross direction and are used to read out the charge through the thin film transistors 32B in an on state are provided on the TFT substrate 30A.

A gate line driver 52A is provided on one side of two adjacent sides of the TFT substrate 30A and a signal processing unit 54A is provided on the other side. Each gate line 34 of the TFT substrate 30A is connected to the gate line driver 52A and each data line 36 of the TFT substrate 30A is connected to the signal processing unit 54A.

The rows of the thin film transistors 32B of the TFT substrate 30A are sequentially turned on by the electric signals which are supplied from the gate line driver 52A through the gate lines 34. Then, the charge which has been read out by the thin film transistor 32B in an on state is transmitted as an electric signal through the data line 36 and is input to the signal processing unit 54A. In this way, charge is sequentially read out from each row of the thin film transistors and image data indicating a two-dimensional radiographic image is acquired.

The signal processing unit 54A includes amplifying circuits (not illustrated) for amplifying an input electric signal and sample-and-hold circuits (not illustrated) which are provided for each data line 36. The electric signal transmitted through each data line 36 is amplified by the amplifying circuit and is then held by the sample-and-hold circuit. A multiplexer and an analog/digital (A/D) converter are connected to the output side of the sample-and-hold circuit in this order. The electric signals held by each sample-and-hold circuit are sequentially (serially) input to the multiplexer and are sequentially selected by the multiplexer. Then, the selected electric signal is converted into digital image data by the A/D converter.

The control unit 58A which will be described below is connected to the signal processing unit MA. The image data output from the A/D converter of the signal processing unit 54A is sequentially output to the control unit 58A. The image memory 56A is connected to the control unit 58A. The image data sequentially output from the signal processing unit 54A is sequentially stored in the image memory 56A under the control of the control unit 58A. The image memory 56A has memory capacity that can store a predetermined amount of image data. Whenever a radiographic image is captured, captured image data is sequentially stored in the image memory 56A.

The control unit 58A includes a central processing unit (CPU) 60, a memory 62 including, for example, a read only memory (ROM) and a random access memory (RAM), and a non-volatile storage unit 64 such as a flash memory. An example of the control unit 58A is a microcomputer.

A communication unit 66 is connected to the control unit 58A and transmits and receives various kinds of information to and from external apparatuses, such as the radiation emitting apparatus 12 and the console 18, using at least one of wireless communication or wired communication. The power supply unit 70 supplies power to each of the above-mentioned various circuits or elements (for example, the gate line driver 52A, the signal processing unit 54A, the image memory 56A, the control unit 58A, and the communication unit 66). In FIG. 3, lines for connecting the power supply unit 70 to various circuits or elements are not illustrated in order to avoid complication.

Components of the TFT substrate 30B, the gate line driver 52B, the signal processing unit 54B, the image memory 56B, and the control unit 58B of the second radiation detector 20B have the same configurations as the corresponding components of the first radiation detector 20A and thus the description thereof will not be repeated here. In addition, the control unit 58A and the control unit 58B are connected such that they can communicate with each other.

With the above-mentioned configuration, the radiography apparatus 16 according to this embodiment captures radiographic images using the first radiation detector 20A and the second radiation detector 20B. Hereinafter, the radiographic image captured by the first radiation detector 20A is referred to as a "first radiographic image" and image data indicating the first radiographic image is referred to as "first radiographic image data". In addition, hereinafter, the radiographic image captured by the second radiation detector 20B is referred to as a "second radiographic image" and image data indicating the second radiographic image is referred to as "second radiographic image data". In addition, in a case in which the "first radiographic image" and the "second radiographic image" are generically referred to, they are simply referred to as "radiographic images" similarly to the above.

Figure 4:
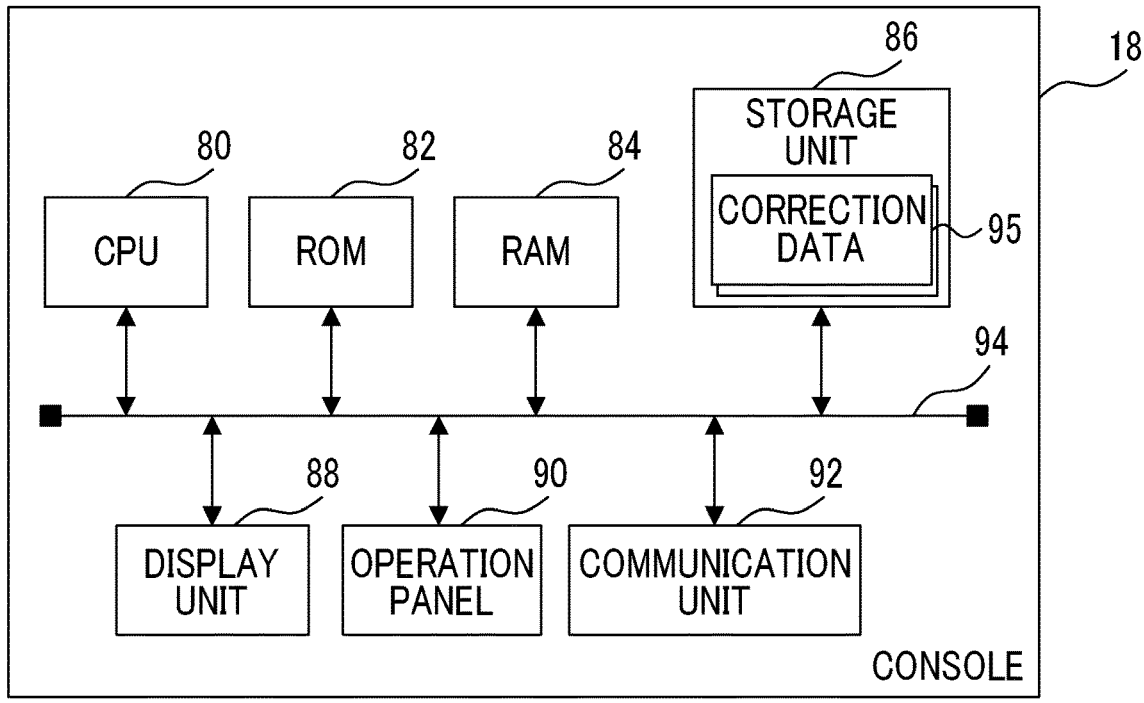
FIG. 4 is a block diagram illustrating an example of the configuration of a main portion of an electric system of a console according to each embodiment.

Next, the configuration of the console 18 according to this embodiment will be described with reference to FIG. 4. As illustrated in FIG. 4, the console 18 comprises a CPU 80 that controls the overall operation of the console 18 and a ROM 82 in which, for example, various programs or various parameters are stored in advance. In addition, the console 18 comprises a RAM 84 that is used as, for example, a work area in a case in which the CPU 80 executes various programs and a non-volatile storage unit 86 such as a hard disk drive (HDD).

The console 18 further comprises a display unit 88 that displays, for example, an operation menu and a captured radiographic image and an operation panel 90 which includes a plurality of keys and to which various kinds of information or operation commands are input. In addition, the console 18 comprises a communication unit 92 that transmits and receives various kinds of information to and from external apparatuses, such as the radiation emitting apparatus 12 and the radiography apparatus 16, or external systems, such as a picture archiving and communication system (PACS) and a radiology information system (RIS), using at least one of wireless communication or wired communication. The CPU 80, the ROM 82, the RAM 84, the storage unit 86, the display unit 88, the operation panel 90, and the communication unit 92 are connected to each other through a bus 94.

A plurality of scattered ray correction data items 95 for correcting scattered rays are stored in the storage unit 86. In addition, the scattered ray correction data 95 will be described in detail below.

In the radiography apparatus 16 according to this embodiment, since the first radiation detector 20A and the radiation limitation member 24 absorb the radiation R, the amount of radiation that reaches the second radiation detector 20B is less than the amount of radiation that reaches the first radiation detector 20A. In addition, the radiation limitation member 24 generally has the characteristic that it absorbs a larger number of soft-ray components than hard-ray components in energy forming the radiation R, which depends on the material forming the radiation limitation member 24. Therefore, the energy distribution of the radiation R that reaches the second radiation detector 20B has a larger number of hard-ray components than the energy distribution of the radiation R that reaches the first radiation detector 20A.

In this embodiment, for example, about 50% of the radiation R that has reached the first radiation detector 20A is absorbed by the first radiation detector 20A and is used to capture a radiographic image. In addition, about 60% of the radiation R that has passed through the first radiation detector 20A and reached the radiation limitation member 24 is absorbed by the radiation limitation member 24. About 50% of the radiation R that has passed through the first radiation detector 20A and the radiation limitation member 24 and reached the second radiation detector 20B is absorbed by the second radiation detector 20B and is used to capture a radiographic image. Since the absorptivity of radiation by the radiation detector 20 and the radiation limitation member 24 varies depending on the energy of the radiation R, the shape of a spectrum changes.

That is, the amount of radiation used by the second radiation detector 20B to capture a radiographic image is about 20% of the amount of radiation used by the first radiation detector 20A to capture a radiographic image. In addition, the ratio of the amount of radiation used by the second radiation detector 20B to capture a radiographic image to the amount of radiation used by the first radiation detector 20A to capture a radiographic image is not limited to the above-mentioned ratio. However, it is preferable that the amount of radiation used by the second radiation detector 20B to capture a radiographic image is equal to or greater than 10% of the amount of radiation used by the first radiation detector 20A to capture a radiographic image in terms of diagnosis.

Figure 5:
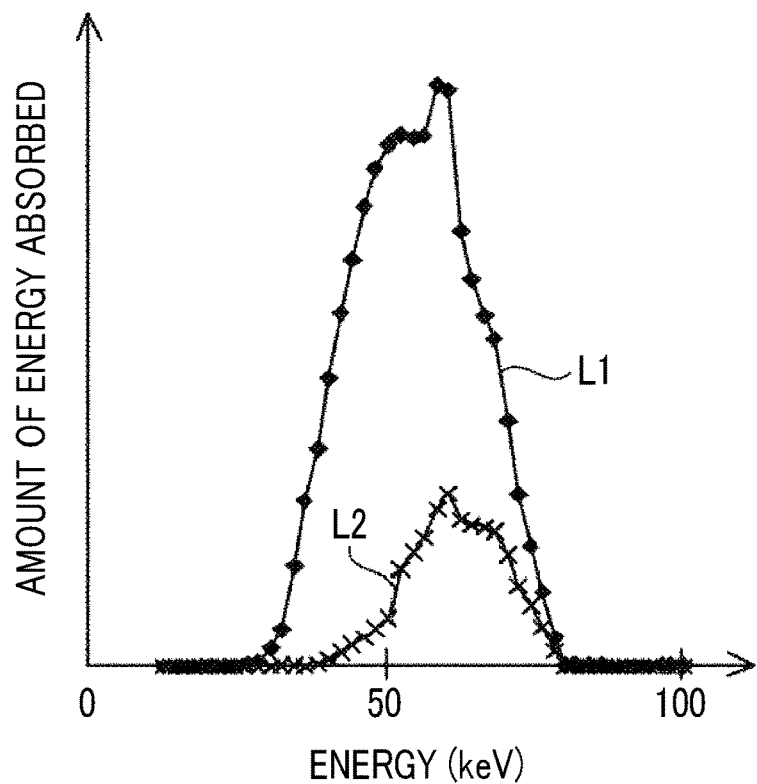
FIG. 5 is a graph illustrating the amount of radiation that reaches each of a first radiation detector and a second radiation detector.

Low-energy components of the radiation R are absorbed first. The radiation R absorbed by each of the first radiation detector 20A and the second radiation detector 20B will be described with reference to FIG. 5. In FIG. 5, the vertical axis indicates the amount of radiation R absorbed and the horizontal axis indicates the energy of the radiation R in a case in which the tube voltage of the radiation source 14 is 80 kV. In addition, in FIG. 5, a solid line L1 indicates the relationship between the energy of the radiation R absorbed by the first radiation detector 20A and the amount of radiation R absorbed. In addition, in FIG. 5, a solid line L2 indicates the relationship between the energy of the radiation R absorbed by the second radiation detector 20B and the amount of radiation R absorbed. Since the low-energy components of the radiation R are absorbed first, for example, as illustrated in FIG. 5, the energy components of the radiation R that reaches the second radiation detector 20B do not include the low-energy components of the energy components of the radiation R that reaches the first radiation detector 20A. That is, the energy of the radiation R emitted to the first radiation detector 20A is different from the energy of the radiation R emitted to the second radiation detector 20B through the first radiation detector 20A. Therefore, in the radiography apparatus 16 according to this embodiment, the radiation detectors 20 are irradiated with the radiations R having different energy levels (radiation R with a first energy level and radiation R with a second energy level) and radiographic images are generated by the radiation detectors 20.

The console 18 according to this embodiment acquires radiographic image data generated by the radiation detectors 20 irradiated with the radiations R having different energy levels. In addition, the console 18 derives the ratio of the values of the corresponding pixels of first radiographic image data and second radiographic image data and generates image data for deriving the bone density of the subject W. Hereinafter, the image data for deriving the bone density of the subject W is referred to as "DXA image data" and an image indicated by the DXA image data is referred to as a "DXA image". Specifically, the console 18 performs log conversion for each pixel value of each of the first radiographic image data and the second radiographic image data. Then, the console 18 generates DXA image data, using an energy subtraction process that subtracts image data obtained by performing log conversion for the second radiographic image data from image data obtained by performing log conversion for the first radiographic image data for each corresponding pixel.

Figure 6:
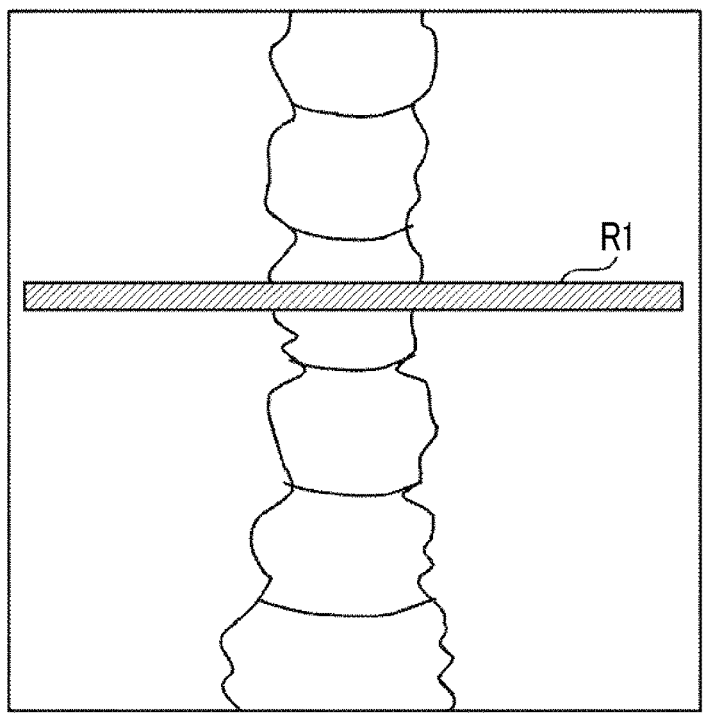
FIG. 6 is a front view illustrating an example of a region from which a DXA profile used to derive bone density is to be derived.

In addition, for example, as illustrated in FIG. 6, the console 18 according to this embodiment derives bone density from each pixel value (that is, the ratio of the values of the corresponding pixels of the first radiographic image and the second radiographic image and a difference value between the pixel values in a log image) of a bone part of the subject W in the cross-sectional direction (the horizontal direction in the example illustrated in FIG. 6) in the DXA image.

Figure 7:
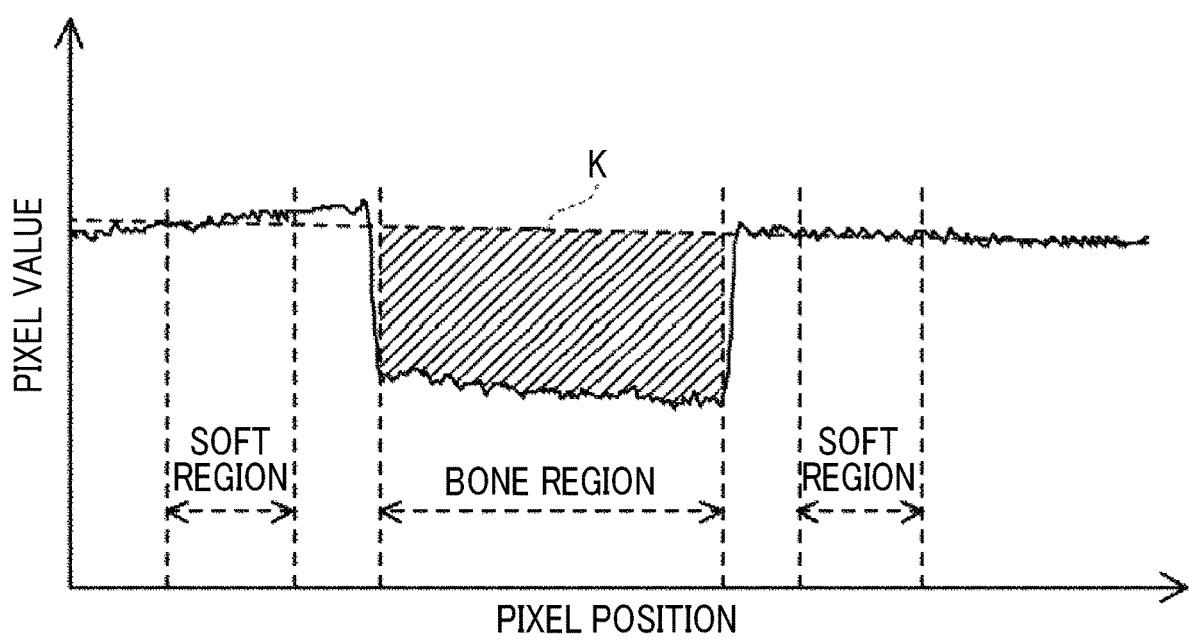
FIG. 7 is a graph illustrating a bone density derivation process.

FIG. 7 illustrates the value of each pixel in a region RI of the DXA image illustrated in FIG. 6. In FIG. 7, the horizontal axis indicates a pixel position in the horizontal direction of FIG. 6. In addition, in FIG. 7, the vertical axis indicates an average value of the values of a plurality of pixels in the vertical direction of FIG. 6 at each pixel position in the horizontal direction of FIG. 6. Hereinafter, a data group of the pixel values at each pixel position along the horizontal direction of FIG. 6 which is illustrated in FIG. 7 is referred to as a "DXA profile".

As illustrated in FIG. 7, for the pixel values in the DXA profile, a pixel value at a pixel position corresponding to the bone tissue of the subject W is less than a pixel value at a pixel position corresponding to the soft tissue. The console 18 according to this embodiment derives the average value of the pixel values in soft tissue regions (hereinafter, referred to as "soft regions") on both sides of a bone tissue region (hereinafter, referred to as a "bone region") and derives a straight line (hereinafter, referred to as a "reference line") K that connects the average values derived at the pixel positions in a central portion of each soft region. In addition, the console 18 adds the differences between the reference line K and the pixel values at each pixel position in the bone region to derive the area of the bone region (the area of a hatched portion illustrated in FIG. 7). The area is a value corresponding to the bone mass of the subject W.

In addition, the console 18 divides the derived area by the number of pixels corresponding to the width of the bone region to derive the difference between the pixel values of the bone region and the soft region per unit number of pixels. The difference is a value corresponding to the bone density of the subject W. Then, the console 18 multiplies the derived difference between the pixel values of the bone region and the soft region per unit number of pixels by a predetermined unit conversion coefficient to derive the bone density of the subject W. In this embodiment, the pixel position of the region R1 used to derive the DXA profile in the DXA image data, the pixel position of the soft region of the DXA profile, and the pixel position of the bone region are predetermined according to, for example, the subject W and an imaging part.

A predetermined amount of scattered rays is removed by the grid 23. However, components (hereinafter, "scattered ray components") caused by the scattered rays which have not been removed by the grid 23 are included in the first radiographic image and the second radiographic image. In particular, in a DXA method for deriving the bone density of the subject W, the numerical value of the derived bone density is also affected by the amount of scattered rays which have not been removed by the grid 23. For this reason, the console 18 according to this embodiment corrects the scattered ray components included in the first radiographic image and the second radiographic image, using the scattered ray correction data 95. In addition, the intensity and spread of the scattered rays vary depending on various conditions. Therefore, in this embodiment, calibration is performed according to various conditions and the scattered ray correction data 95 obtained by the calibration is stored in the storage unit 86 so as to be associated with each combination of the conditions. Hereinafter, the calibration will be described in detail.

Figure 8A:
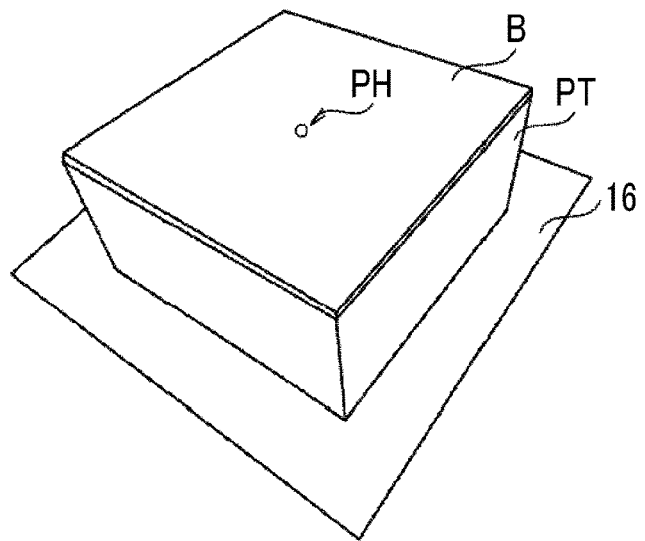
FIG. 8A is a perspective view illustrating calibration according to each embodiment.

The scattered ray correction data 95 according to this embodiment will be described with reference to FIGS. 8A to 9B. In this embodiment, as illustrated in FIG. 8A, a plurality of scattered ray correction data items 95 which have been obtained in advance by calibration using a phantom PT simulating the human body and a flat-plate-shaped radiation shielding member B shielding the radiation R are stored in the storage unit 86. A pinhole PH is formed in a central portion of the radiation shielding member B. The phantom PT simulates the human body using a material corresponding to the soft tissues of the human body and a material corresponding to the bone tissues of the human body. For example, acryl or urethane can be applied as the material corresponding to the soft tissues of the human body. In addition, for example, hydroxyapatite can be applied as the material corresponding to the bone tissues of the human body. Hereinafter, the scattered ray correction data 95 will be described in detail.

Figure 8B:
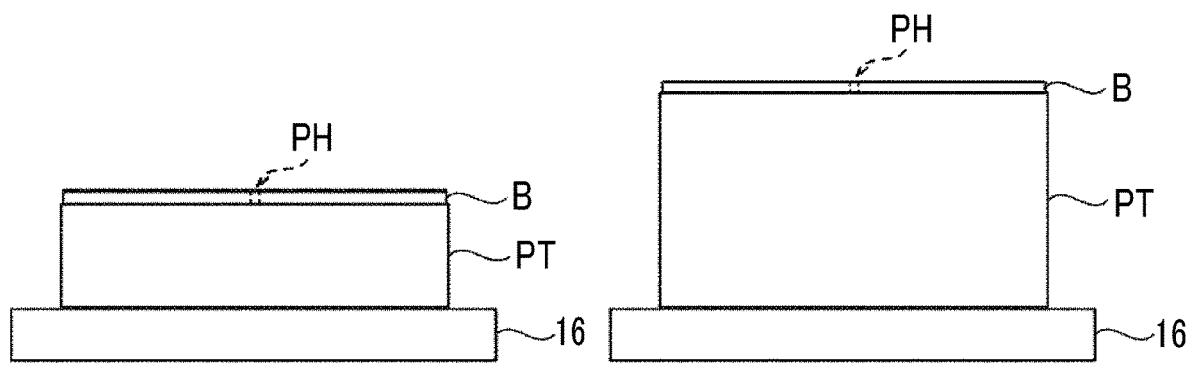
FIG. 8B is a side view illustrating calibration in a subject region according to each embodiment.

In each radiation detector 20, different scattered rays are generated in a region (hereinafter, referred to as a "subject region") irradiated with the radiation R that has been transmitted through the subject W and a region (hereinafter, referred to as a "directly irradiated region") directly irradiated with the radiation R that has not been transmitted through the subject W. Therefore, in this embodiment, for calibration related to the subject region, as illustrated in FIG. 8B, the phantom PT is disposed on the side of the radiography apparatus 16 on which the radiation R is incident, the radiation shielding member B is disposed on the side of the phantom PT on which the radiation R is incident, and the radiation R is emitted from the radiation emitting apparatus 12 for a predetermined period. The console 18 generates the scattered ray correction data 95 with image data obtained from each radiation detector 20 in this case and stores the generated scattered ray correction data 95 in the storage unit 86.

Figure 9A:
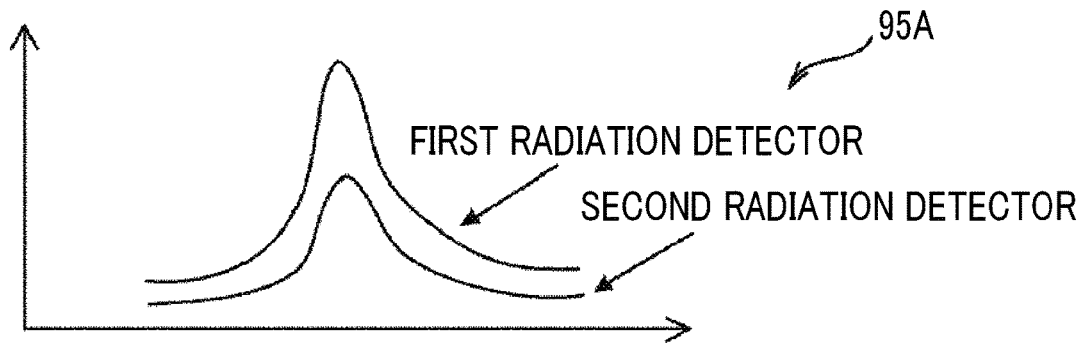
FIG. 9A is a graph illustrating an example of scattered ray correction data according to the first embodiment.
Figure 9B:
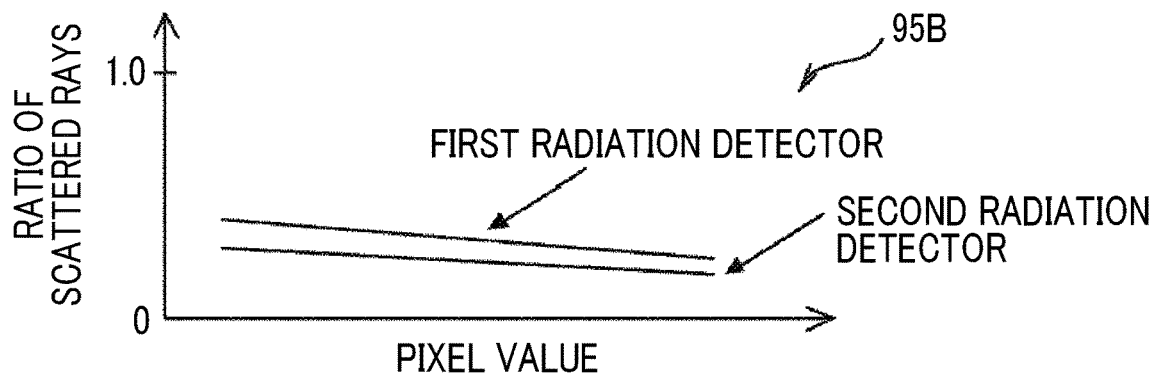
FIG. 9B is a graph illustrating an example of the scattered ray correction data according to the first embodiment.

For example, the scattered ray correction data 95 corresponding to the subject region includes information indicating the spread of scattered rays illustrated in FIG. 9A and information indicating the intensity of scattered rays illustrated in FIG. 9B. The information indicating the spread of scattered rays illustrated in FIG. 9A is also referred to as a point spread function (PSF). In addition, the information indicating the intensity of scattered rays illustrated in FIG. 9B is information in which a pixel value per unit amount of radiation is associated with the ratio of scattered rays at the pixel value. Hereinafter, in the scattered ray correction data 95, the information indicating the spread of scattered rays is referred to as a PSF 95A and the information indicating the intensity of scattered rays is referred to intensity information 95B.

As described above, the energy of the radiation R emitted to the first radiation detector 20A is different from the energy of the radiation R emitted to the second radiation detector 20B. Therefore, as illustrated in FIGS. 9A and 9B, the information indicating the spread of scattered rays and the information indicating the intensity of scattered rays are different in the first radiation detector 20A and the second radiation detector 20B. For this reason, in this embodiment, the scattered ray correction data 95 obtained from the first radiation detector 20A by calibration is stored in the storage unit 86 so as to be associated with the first radiation detector 20A. In addition, the scattered ray correction data 95 obtained from the second radiation detector 20B by calibration is stored in the storage unit 86 so as to be associated with the second radiation detector 20B.

In the subject region, different scattered rays are generated according to the body thickness of the subject W. Therefore, in this embodiment, as illustrated in FIG. 8B, the scattered ray correction data 95 obtained by calibration using the phantoms PT with a plurality of types of body thicknesses is stored in the storage unit 86 so as to be associated with each body thickness.

Figure 8C:
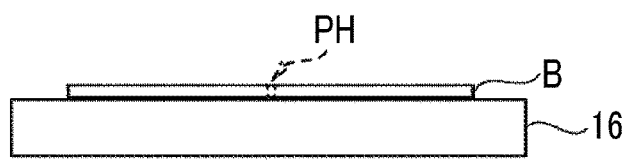
FIG. 8C is a side view illustrating calibration in a directly irradiated region according to each embodiment.

In contrast, for calibration related to the directly irradiated region, as illustrated in FIG. 8C, the radiation shielding member B is disposed on the side of the radiography apparatus 16 on which the radiation R is incident and the radiation R is emitted from the radiation emitting apparatus 12 for a predetermined period. The console 18 derives information indicating the spread of scattered rays, using image data obtained from each radiation detector 20 in this case. In addition, the console 18 derives the amount of scattered rays from the amount of radiation and derives the amount of scattered rays per unit amount of radiation as information indicating the intensity of scattered rays. Then, the console 18 stores the derived information indicating the spread of scattered rays and the derived information indicating the intensity of scattered rays as the scattered ray correction data 95 corresponding to the directly irradiated region in the storage unit 86.

In addition, different scattered rays are generated according to imaging conditions. Therefore, in this embodiment, calibration is performed each of the imaging conditions used in the facility in which the radiography system 10 is provided and the scattered ray correction data 95 is stored in the storage unit 86 so as to be associated with the imaging conditions. The imaging conditions include, for example, a material (for example, tungsten) forming a bulb of the radiation source 14, a tube voltage, a material (for example, copper) forming the radiation limitation member 24, the characteristics of the grid 23 (for example, a grid ratio, grid density, and a convergence distance), and a source image distance (SID). The SID indicates a distance from the radiation source 14 to a surface for detecting the radiation R in the first radiation detector 20A. In addition, the imaging conditions include the quality of a material (for example, carbon) forming the surface of a case accommodating the radiography apparatus 16 on which the radiation R is incident. Examples of the surface of the case accommodating the radiography apparatus 16 on which the radiation R is incident include a top plate of a decubitus imaging table and a decorative cover of an upright imaging table.

Figure 10:
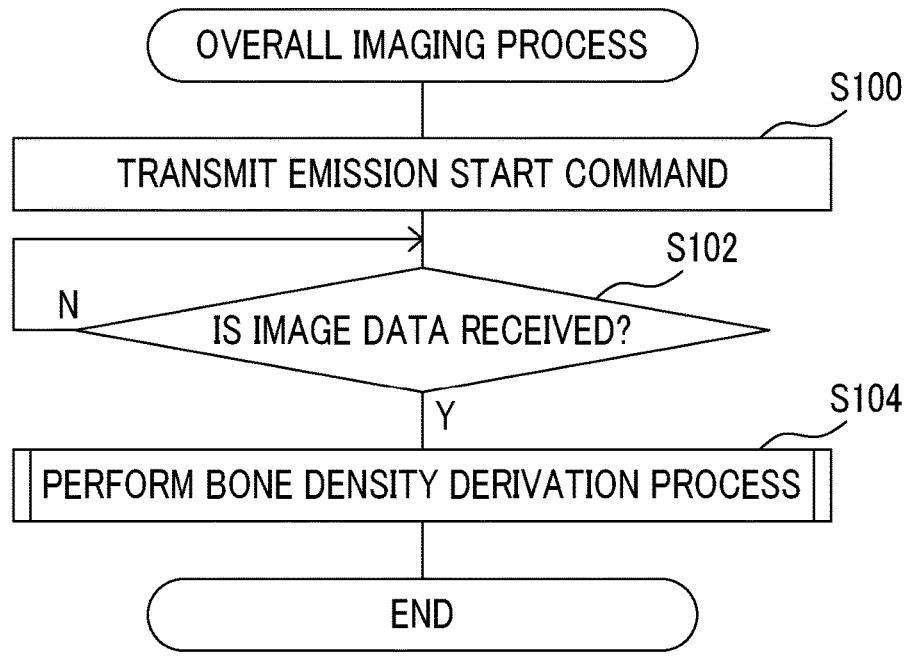
FIG. 10 is a flowchart illustrating an example of an overall imaging process according to the first embodiment.

Next, the operation of the radiography system 10 according to this embodiment will be described. FIG. 10 is a flowchart illustrating the process flow of an overall imaging processing program executed by the CPU 80 of the console 18 in a case in which the user inputs the name of the subject W, an imaging part, and an imaging menu through the operation panel 90. The overall imaging processing program is installed in the storage unit 86 of the console 18 in advance.

Figure 11:
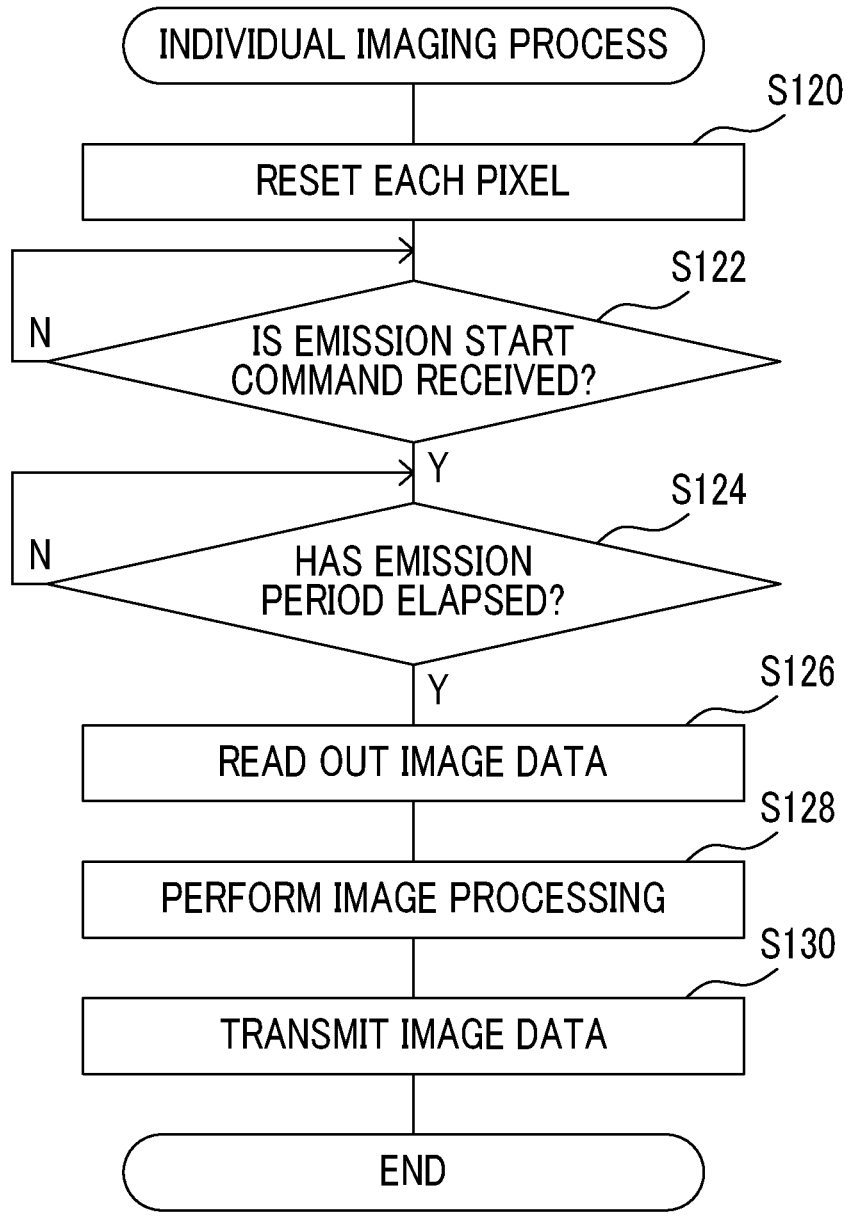
FIG. 11 is a flowchart illustrating an example of an individual imaging process according to the first embodiment.

FIG. 11 is a flowchart illustrating the process flow of an individual imaging processing program executed by the control unit 58A of the radiography apparatus 16 in a case in which the radiography apparatus 16 is turned on. The individual imaging processing program is installed in the ROM of the memory 62 of the control unit 58A in advance. In addition, the individual imaging processing program is installed in the ROM of the memory 62 of the control unit 58B in advance and is executed by the control unit 58B of the radiography apparatus 16 in a case in which the radiography apparatus 16 is turned on. In the individual imaging process illustrated in FIG. 11, the control unit 58A and the control unit 58B perform the same process. Therefore, hereinafter, only a case in which the individual imaging process is performed by the control unit 58A will be described and the description of a case in which the individual imaging process is performed by the control unit 58B will be omitted.

In Step S100 illustrated in FIG. 10, the CPU 80 transmits information included in the input imaging menu to the radiography apparatus 16 through the communication unit 92 and transmits the emission conditions of the radiation R to the radiation emitting apparatus 12 through the communication unit 92. Then, the CPU 80 transmits a command to start the emission of the radiation R to the radiography apparatus 16 and the radiation emitting apparatus 12 through the communication unit 92. In a case in which the emission conditions and the emission start command transmitted from the console 18 are received, the radiation emitting apparatus 12 starts the emission of the radiation R according to the received emission conditions. The radiation emitting apparatus 12 may include an irradiation button. In this case, the radiation emitting apparatus 12 receives the emission conditions and the emission start command transmitted from the console 18 and starts the emission of the radiation R according to the received emission conditions in a case in which the irradiation button is pressed.

In the next Step S102, the CPU 80 waits until the first radiographic image data of the first radiographic image captured by the first radiation detector 20A and the second radiographic image data of the second radiographic image captured by the second radiation detector 20B are received. In a case in which the CPU 80 receives the first radiographic image data and the second radiographic image data through the communication unit 92, the determination result in Step S102 is "Yes" and the process proceeds to Step S104.

Figure 12:
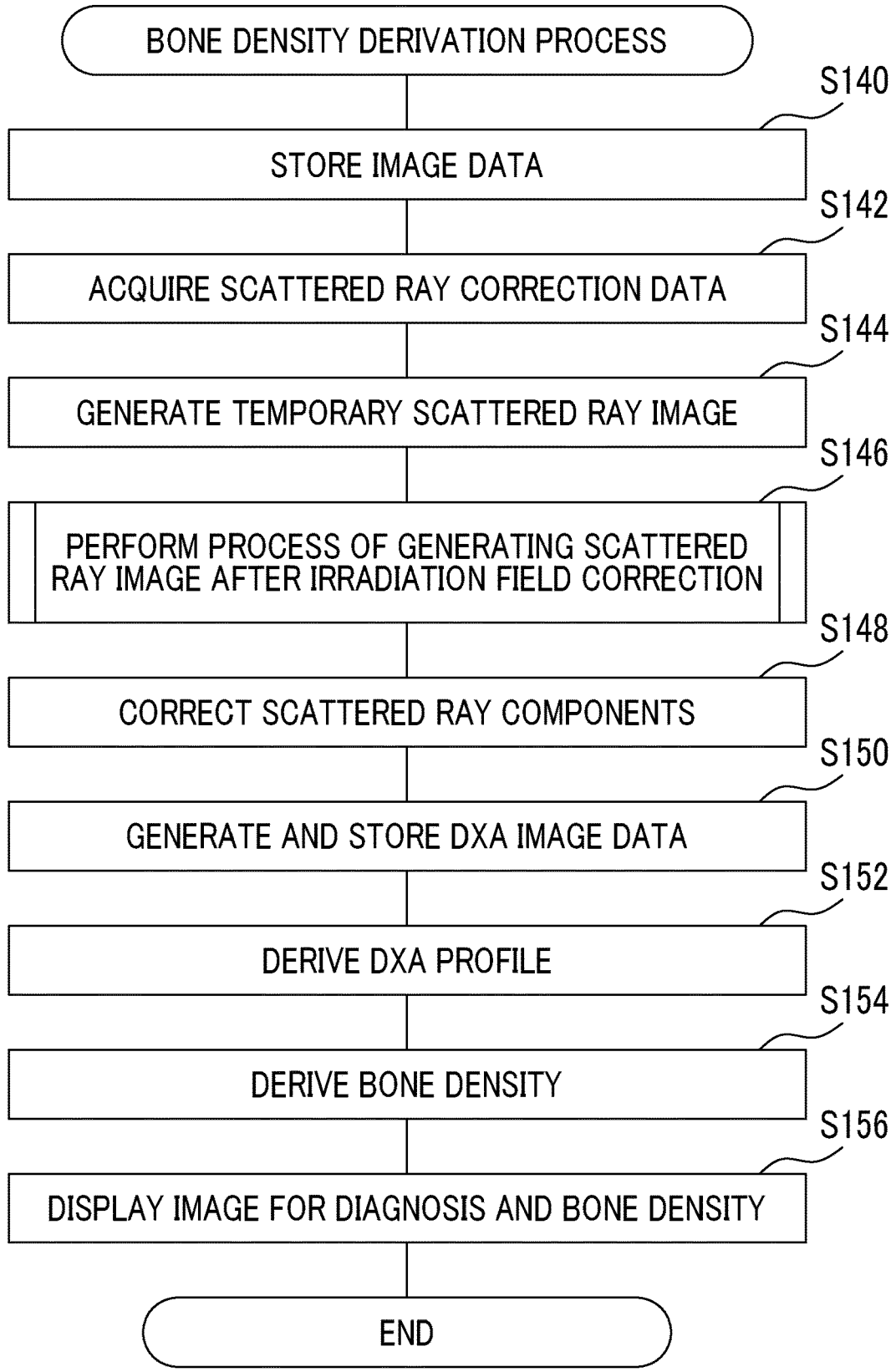
FIG. 12 is a flowchart illustrating an example of a bone density derivation process according to the first embodiment.

In Step S104, the CPU 80 performs a bone density derivation process whose example is illustrated in FIG. 12 and then ends the overall imaging process.

In Step S120 of the individual imaging process illustrated in FIG. 11, the control unit 58A performs a reset operation which emits the charge accumulated in the sensor unit 32A of each pixel 32 in the first radiation detector 20A. In addition, the control unit 58A may perform the reset operation in Step S120 only once, may repeatedly perform the reset operation a predetermined number of times or at a predetermined time interval, or may repeatedly perform the reset operation until the determination result in Step S122, which will be described below, becomes "Yes".

In Step S122, the control unit 58A is in a standby state until a command to start the emission of the radiation R is received. In a case in which the control unit 58A receives the emission start command transmitted from the console 18 in Step S100 of the overall imaging process through the communication unit 66, the determination result in Step S122 is "Yes" and the process proceeds to Step S124. In a case in which the radiation emitting apparatus 12 comprises an irradiation button and the control unit 58A receives the emission start command transmitted from the console 18 and information indicating that the irradiation button has been pressed through the communication unit 66, the determination result in Step S122 is "Yes". For example, in a case in which the irradiation button is pressed, the radiation emitting apparatus 12 may directly transmit information indicating that the irradiation button has been pressed to the radiography apparatus 16 or may transmit the information to the radiography apparatus 16 through the console 18.

In Step S124, the control unit 58A waits for an emission period that is included in the information transmitted from the console 18 in Step S100 of the overall imaging process. Specifically, the determination result in Step S124 is "No" until the emission period elapses. In a case in which the emission period comes, the determination result in Step S124 is "Yes" and the process proceeds to Step S126.

In Step S126, the control unit 58A controls the gate line driver 52A such that the gate line driver 52A sequentially outputs an on signal to each of the gate lines 34 of the first radiation detector 20A for a predetermined period. Then, the rows of the thin film transistors 32B connected to each gate line 34 are sequentially turned on and the charge accumulated in each sensor unit 32A in each row sequentially flows as an electric signal to each data line 36. Then, the electric signal which has flowed to each data line 36 is converted into digital image data by the signal processing unit 54A and is stored in the image memory 56A.

Then, in Step S128, the control unit 58A performs image processing for performing various types of correction, such as offset correction and gain correction, for the image data stored in the image memory 56A in Step S126. Then, in Step S130, the control unit 58A transmits the image data (first radiographic image data) subjected to the image processing in Step S128 to the console 18 through the communication unit 66 and then ends the individual imaging process.

In a case in which the console 18 receives the first radiographic image data and the second radiographic image data transmitted by the process in Step S130, the determination result in Step S102 of the overall imaging process (see FIG. 10) is "Yes" and the process proceeds to Step S104. Then, the bone density derivation process illustrated in FIG. 12 is performed.

In Step S140 of the bone density derivation process illustrated in FIG. 12, the CPU 80 stores the first radiographic image data and the second radiographic image data received in Step S102 of the overall imaging process (see FIG. 10) in the storage unit 86.

Then, in Step S142, the CPU 80 acquires the scattered ray correction data 95 associated with the imaging conditions and the first radiation detector 20A from the storage unit 86. In addition, the CPU 80 acquires the scattered ray correction data 95 associated with the imaging conditions and the second radiation detector 20B from the storage unit 86. Further, for example, the console 18 may acquire the scattered ray correction data 95 from an external system connected through the network.

Then, in Step S144, the CPU 80 generates image data indicating a temporary scattered ray image for the first radiographic image, using the scattered ray correction data 95 associated with the imaging conditions and the first radiation detector 20A. Specifically, the CPU 80 derives the amount and spread of scattered rays for each pixel of the first radiographic image, using the scattered ray correction data 95, and performs a convolution operation for the derived amount and spread of scattered rays to generate image data indicating a temporary scattered ray image.

In addition, similarly, the CPU 80 generates image data indicating a temporary scattered ray image, using the scattered ray correction data 95 associated with the imaging conditions and the second radiation detector 20B, for the second radiographic image.

Figure 13:
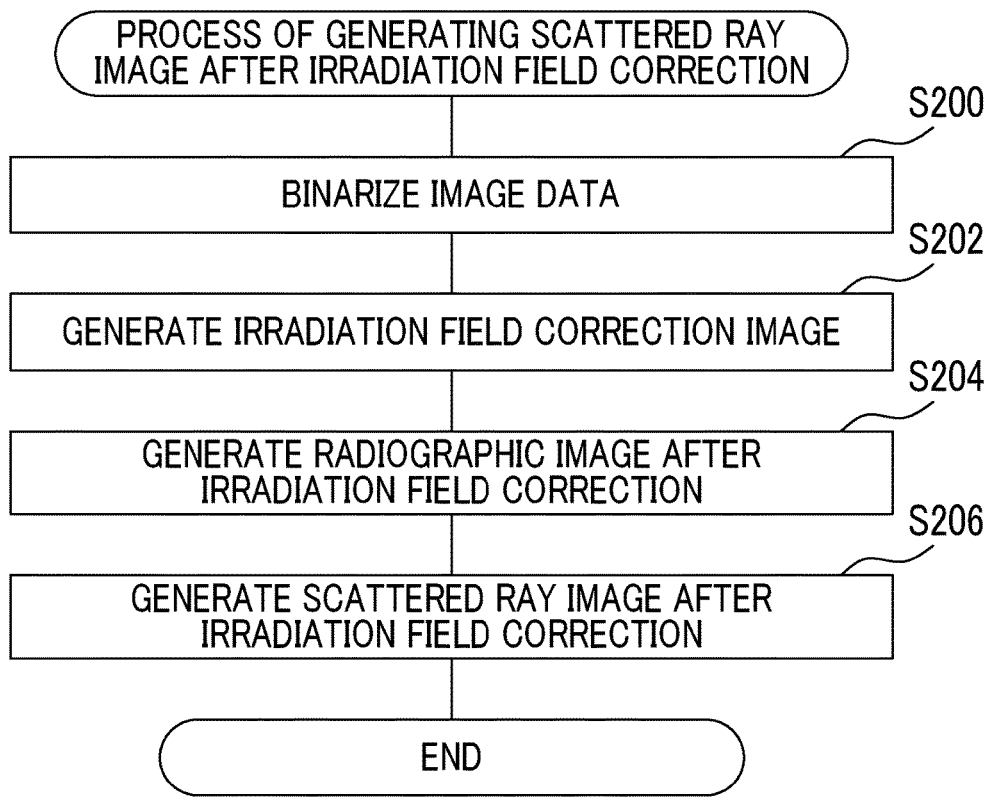
FIG. 13 is a flowchart illustrating an example of a process of generating a scattered ray image after irradiation field correction according to the first embodiment.
Figure 14:
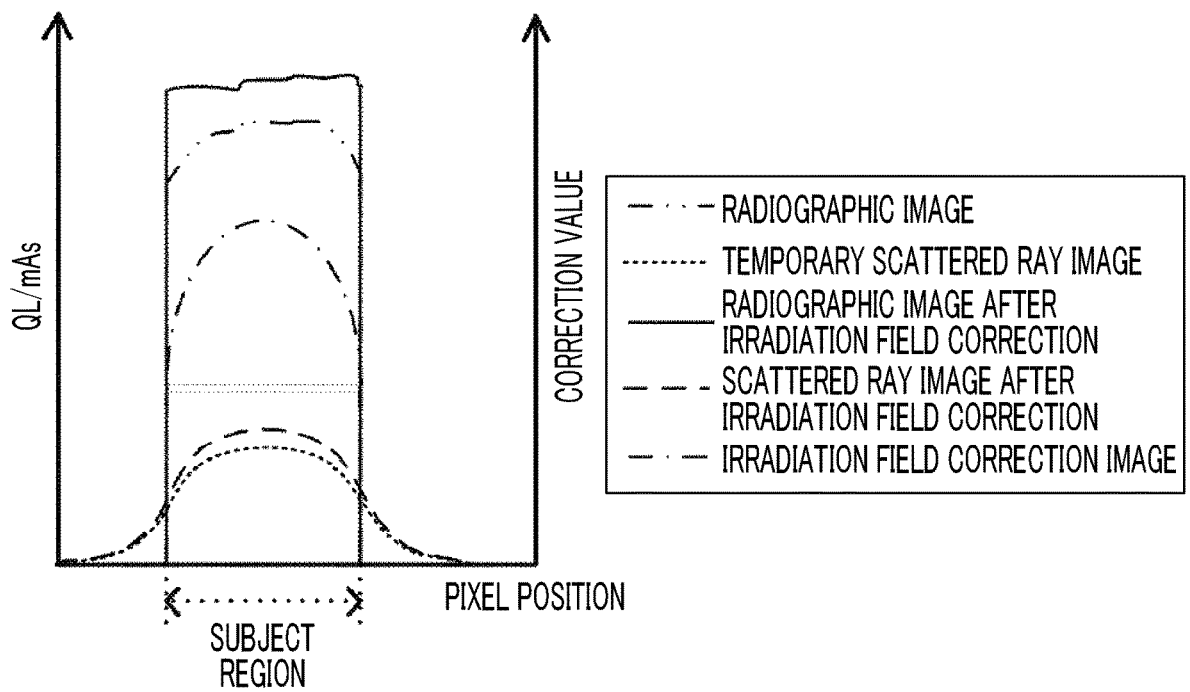
FIG. 14 is a graph illustrating an example of a profile of various images generated in the process of generating the scattered ray image after irradiation field correction according to the first embodiment.

Then, in Step S146, the CPU 80 performs a process of generating a scattered ray image after irradiation field correction, an example of which is illustrated in FIG. 13. The process of generating the scattered ray image after irradiation field correction performed in the CPU 80 according to this embodiment will be described with reference to FIGS. 13 to 15. FIG. 13 is a flowchart illustrating an example of the process of generating the scattered ray image after irradiation field correction. FIG. 14 is a graph illustrating an example of the profile of various images generated in the process of generating the scattered ray image after irradiation field correction. In addition, FIG. 15 is a diagram schematically illustrating an example of the relationship between various images generated in the process of generating the scattered ray image after irradiation field correction.

A temporary scattered ray image is generated using the scattered ray correction data 95 in order to remove scattered rays from the image, as described above. However, since the radiographic image includes a scattered ray component, the scattered ray correction data 95 is applied to the image which has already been blurred by the scattered radiation component in the generation of the temporary scattered ray image. Therefore, as illustrated in the profile of the radiographic image which is illustrated as an example in FIG. 14, in a region (a region having one side that scattering rays reach and the other side that scattering rays do not reach) in which scattered rays are anisotropic, such as the boundary of the irradiation field, the shape of the profile causes an end sag structure. In addition, the "end sag structure" indicates a state in which a pixel value (QL/mAs) per unit is not suddenly changed in a region in which the first radiation detector 20A (second radiation detector 20B) is irradiated with radiation transmitted through the subject W, that is, a subject region and a region other than the subject region. Since the profile of the radiographic image causes the end sag structure, the estimation of the scattered ray component may be unstable.

For this reason, in this embodiment, the scattered ray image after irradiation field correction which has been corrected on the basis of the information of the region in which scattered rays are anisotropic, such as the irradiation field, that is, the information of the subject region indicating a region of the first radiation detector 20A (second radiation detector 20B) irradiated with radiation transmitted through the subject W is generated. Since the scattered ray component is corrected using the scattered ray image after irradiation field correction, instead of the temporary scattered ray image, the scattered ray component from which the influence of the end sag structure has been removed is corrected.

Figure 15:
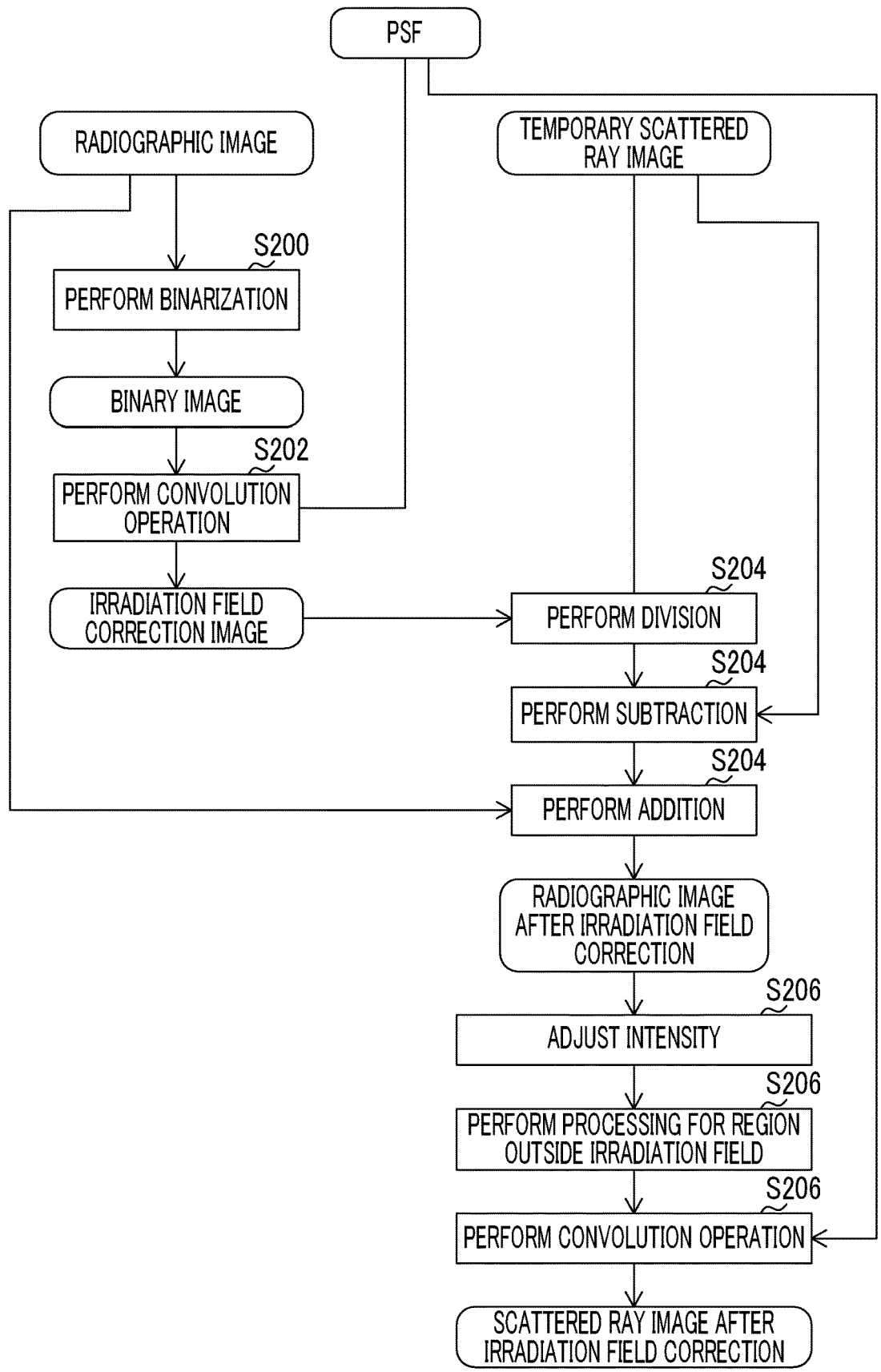
FIG. 15 is a diagram schematically illustrating an example of the relationship between various images generated in the process of generating the scattered ray image after irradiation field correction according to the first embodiment.

First, in Step S200 illustrated in FIG. 13, the CPU 80 binarizes each of the first radiographic image data and the second radiographic image data to generate each binary image as also illustrated in FIG. 15. Specifically, the CPU 80 reads the first radiographic image data and the second radiographic image data from the storage unit 86 and binarizes the pixel values of each radiographic image on the basis of a predetermined threshold value. As can be seen from the profile illustrated in FIG. 14, the pixel value per unit is "0" in a region other than the subject region. Therefore, the binarization makes it possible to simply derive the subject region, that is, to create an irradiation field map. In addition, for example, the threshold value used to binarize the pixel value may be experimentally obtained in advance. The information of the binary image generated in this step is an example of region information according to the present disclosure and is image information obtained by binarizing the pixel values of the radiographic image. Even in a case in which the boundary of the irradiation field is not included in the radiographic image, the irradiation field is generally finite. In general, since the irradiation field has the same size as the radiation detector, it is considered that the end sag structure is generated. In this embodiment, it is considered that the position of the boundary of the irradiation field is matched with the position of the end of the radiographic image. Therefore, the convolution operation is applied assuming that the pixel value outside the radiographic image is "0".

Then, in Step S202, the CPU 80 generates an image for correcting the irradiation field (irradiation field correction image) corresponding to each of the first radiographic image and the second radiographic image. Specifically, as illustrated in FIG. 15, the CPU 80 performs a convolution operation for each of the binary image of the first radiographic image and the binary image of the second radiographic image generated in Step S200 with the PSF 95A to generate image data indicating a scattered ray image caused by the subject region as image data of the irradiation field correction image as in the generation of the temporary scattered ray image. As illustrated in the profile of the irradiation field correction image in FIG. 14, in the irradiation field correction image, the end sag structure is improved as compared to the radiographic image. In a case in which the radiographic image is represented by A, the binarized radiographic image is represented by A2, the PSF 95A is represented by B, and the irradiation field correction image is represented by A2B, the reciprocal of A2B is a coefficient for correcting the end sag structure. This coefficient is not derived at one point, but is derived at each point in a two-dimensional system.

As such, in this embodiment, the influence of the irradiation field is derived by the process in Steps S200 and S202.

Then, in Step S204, the CPU 80 generates radiographic images after the irradiation field is corrected (radiographic images after irradiation field correction) which correspond to the first radiographic image and the second radiographic image. Specifically, as illustrated in FIG. 15, the CPU 80 generates the radiographic image after irradiation field correction by dividing each pixel value of the temporary scattered ray image generated in Step S144 by each pixel value of the irradiation field correction image, subtracting each pixel value of the temporary scattered ray image from each calculated pixel value, and adding each pixel value of the radiographic image to each calculated pixel value. In a case in which the temporary scattered ray image is represented by AB, the radiographic image after irradiation field correction is represented by A+AB/A2B−AB. As illustrated in the profile of the radiographic image after irradiation field correction in FIG. 14, the radiographic image after irradiation field correction is a virtual image indicating a case in which there is no end sag structure caused by the irradiation field.

As such, in this embodiment, the influence of the irradiation field is excluded from the radiographic image by the process in Step S204.

Then, in Step S206, the CPU 80 generates scattered ray images after irradiation field correction corresponding to the first radiographic image and the second radiographic image and ends the process of generating the scattered ray image after irradiation field correction. Specifically, as illustrated in FIG. 15, the CPU 80 adjusts intensity according to the mAs value using the intensity information 95B, performs processing for a region outside the irradiation field on the basis of an image indicating a human body area or the edge of the irradiation field, and performs a convolution operation according to the mAs value using the PSF 95A to generate the image data of a scattered ray image after irradiation field correction as in the generation of the temporary scattered ray image.

As such, in this embodiment, a scattered ray component is calculated again by the process in Step S206. In a case in which the intensity coefficient is represented by r, the scattered ray image after irradiation field correction is represented by the following Expression (1):

$$A - \{A + (AB \times r \times 1/A2B) - AB \times r\} B \times r \qquad (1).$$

As can be seen from the comparison between the profile of the temporary scattered ray image illustrated in FIG. 14 and the profile of the scattered ray image after irradiation field correction, the scattered ray image after irradiation field correction becomes a scattered ray image with higher accuracy than the temporary scattered ray image.

In addition, in a case in which the scattered ray component of the radiographic image is corrected by the temporary scattered ray image unlike this embodiment, if an image obtained by the phantom PT without the pinhole PH is represented by A, the pixel value of the image is represented by Ai, the pixel value of the image AB obtained by performing a convolution operation using the PSF 95A is represented by ABi, and the pixel value of an image obtained by the phantom PT with the pinhole PH is represented by Ci, an intensity coefficient r0 for the pixel value Ai is represented by the following Expression (2):

$$r0 = (Ai - Ci)/ABi \quad (2).$$

In this embodiment, since the image A obtained by the phantom PT is replaced with an image without the end sag structure, the intensity coefficient r is represented by the following Expression (3):

$$r = \{Ai + ABi/A2Bi - Abi - Ci\}/\{(A + AB/A2B - AB)B\}i \quad (3).$$

That is, at the intensity coefficient r according to this embodiment, in a case in which A2Bi is represented by β and Ai-Ci is represented by a, a temporary pixel value is multiplied by $β+α(1-β)$ and the original ratio is multiplied by $β/\{β+α(1-β)\}$. As such, the intensity coefficient r in a case in which there is no end sag structure, that is, the irradiation field is infinite and there is no dependence of the irradiation field is derived from the data of the finite irradiation field.

As such, in a case in which Step S146 of the bone density derivation process ends, in Step S148, the CPU 80 subtracts image data indicating the scattered ray image after irradiation field correction generated from the first radiographic image in Step S146 from the first radiographic image data for each corresponding pixel to correct the scattered ray components of the first radiographic image. In addition, the CPU 80 subtracts image data indicating the scattered ray image after irradiation field correction generated from the second radiographic image in Step S146 from the second radiographic image data for each corresponding pixel to correct the scattered ray components of the second radiographic image.

Then, in Step S150, the CPU 80 generates DXA image data, using the corrected first radiographic image data and second radiographic image data subjected to the correction in Step S148. In a case in which the first radiographic image data and the second radiographic image data are simply referred to in Steps S150 to S156, it is assumed that the first radiographic image data and the second radiographic image data indicate the corrected first radiographic image data and second radiographic image data subjected to the correction in Step S148, respectively.

The CPU 80 performs log conversion for each pixel value of each of the first radiographic image data and the second radiographic image data. Then, the CPU 80 generates DXA image data, using an energy subtraction process that subtracts image data obtained by performing log conversion for the second radiographic image data from image data obtained by performing log conversion for the first radiographic image data for each corresponding pixel. Then, the CPU 80 stores the generated DXA image data in the storage unit 86.

A method for determining the corresponding pixels of the first radiographic image data and the second radiographic image data is not particularly limited. For example, the amount of positional deviation between first radiographic image data and second radiographic image data is calculated from a difference in the position of a marker between the first radiographic image data and the second radiographic image data captured by the radiography apparatus 16 in a state in which the marker is placed in advance. Then, the corresponding pixels of the first radiographic image data and the second radiographic image data are determined on the basis of the calculated amount of positional deviation.

In this case, for example, the amount of positional deviation between first radiographic image data and second radiographic image data may be calculated from a difference in the position of a marker between the first radiographic image data and the second radiographic image data obtained by capturing the image of the marker together with the subject W in a case in which the image of the subject W is captured. In addition, for example, the amount of positional deviation between first radiographic image data and second radiographic image data may be calculated on the basis of the structure of the subject in the first radiographic image data and the second radiographic image data obtained by capturing the image of the subject W.

Then, in Step S152, the CPU 80 derives a DXA profile using the DXA image data generated in Step S150. Then, in Step S154, the CPU 80 derives an integrated value of the differences between the reference line K and the pixel values of the bone region in the DXA profile derived in Step S152. In addition, the CPU 80 divides the derived integrated value by the number of pixels corresponding to the width of the bone region in the DXA profile. Then, the CPU 80 multiplies the value obtained by the division by a unit conversion coefficient to derive the bone density of the subject W.

Then, in Step S156, the CPU 80 displays the first radiographic image indicated by the first radiographic image data as an image for diagnosis on the display unit 88 and displays the bone density derived in Step S154 on the display unit 88. Then, the CPU 80 ends the bone density derivation process.

In addition, the CPU 80 may generate image data (hereinafter, referred to as "ES image data") indicating an energy subtraction image (hereinafter, referred to as an "ES image"), using the corrected first radiographic image data and second radiographic image data subjected to the correction in Step S148. In this case, for example, the CPU 80 subtracts image data obtained by multiplying the first radiographic image data by a predetermined coefficient from image data obtained by multiplying the second radiographic image data by a predetermined coefficient for each corresponding pixel. The CPU 80 generates ES image data indicating an ES image in which the soft tissues have been removed and the bone tissues have been highlighted, using the subtraction. In this example, in Step S156, the CPU 80 may display an ES image in which the bone tissues have been highlighted on the display unit 88, instead of the image for diagnosis.

In addition, the CPU 80 may specify the edge of a bone region from the ES image in which the bone tissues have been highlighted and may use the specification result as a pixel position corresponding to the bone region in the DXA image data. In this case, for example, the CPU 80 estimates the approximate range of the bone region on the basis of the imaging part included in the imaging menu. Then, the CPU 80 detects pixels that are disposed in the vicinity of the pixels, of which the differential values are equal to or greater than a predetermined value, as the pixels forming the edge (end) of the bone region in the estimated range to specify the bone region.

In this case, the CPU 80 may specify, as the soft region, a region which has a predetermined area including pixels that are separated from the specified edge of the bone region by a distance corresponding to a predetermined number of pixels in a predetermined direction in which the region becomes further away from the bone part. In this case, the CPU 80 may use the specification result as a pixel position corresponding to the soft tissue in the DXA image data.

As such, in this embodiment, the console 18 generates a scattered ray image after irradiation field correction for correcting the scattered ray components of the radiographic image according to the subject region, using the scattered ray correction data 95, and corrects the scattered ray components of the radiographic image, using the scattered ray image after irradiation field correction. Therefore, according to this embodiment, it is possible to correct components caused by the scattered rays of the radiation R included in the radiographic image with high accuracy.

Second Embodiment

Hereinafter, a second embodiment of the present disclosure will be described in detail. Since the configuration of a radiography system 10 according to this embodiment is the same as that in the first embodiment (see FIG. 1, FIG. 3, and FIG. 4) except the configuration of a radiography apparatus 16, the description thereof will not be repeated here. In addition, components having the same functions as those in the first embodiment are denoted by the same reference numerals and the description thereof will not be repeated.

Figure 16:
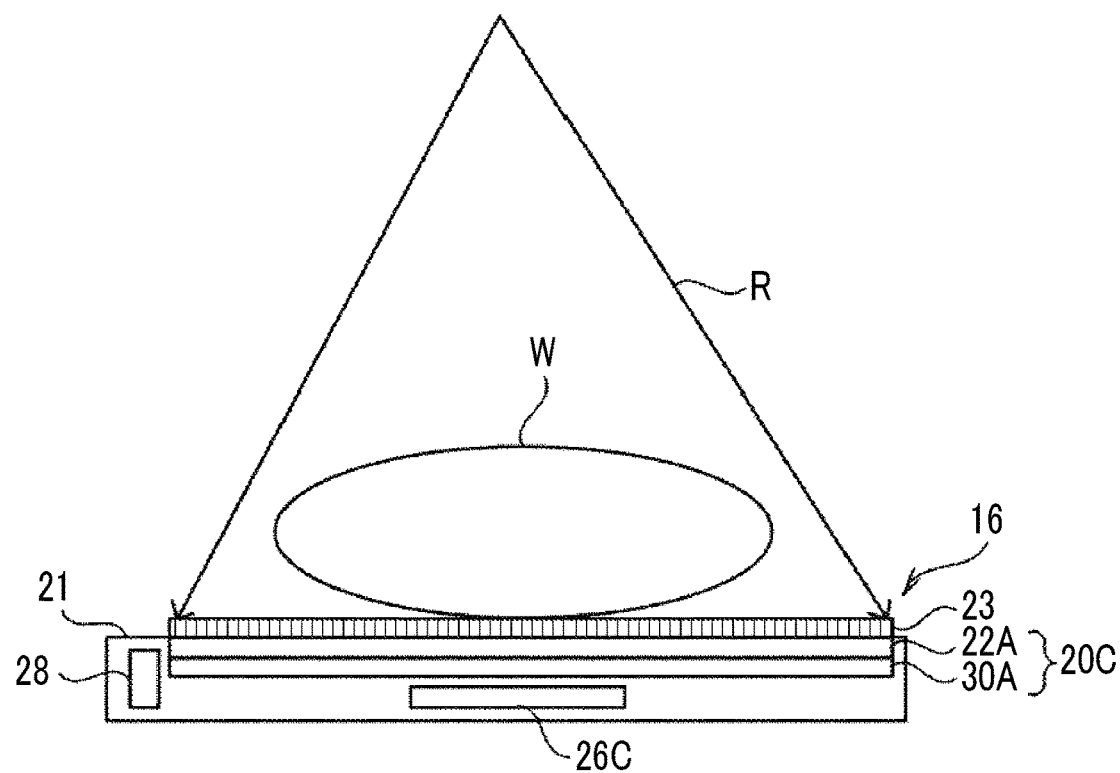
FIG. 16 is a side cross-sectional view illustrating an example of the configuration of a radiography apparatus according to a second embodiment.

As illustrated in FIG. 16, a radiation detector 20C that detects radiation R transmitted through a subject W and a control substrate 26C are provided in the housing 21 of the radiography apparatus 16 according to this embodiment. Since the configuration of the radiation detector 20C is the same as that of the first radiation detector 20A according to the first embodiment, the description thereof will not be repeated here. In addition, since the configuration of the control substrate 26C is the same as that of the control substrate 26A according to the first embodiment, the description thereof will not be repeated here. A grid 23 for removing scattered rays is provided between the housing 21 and the subject W.

Figure 17:
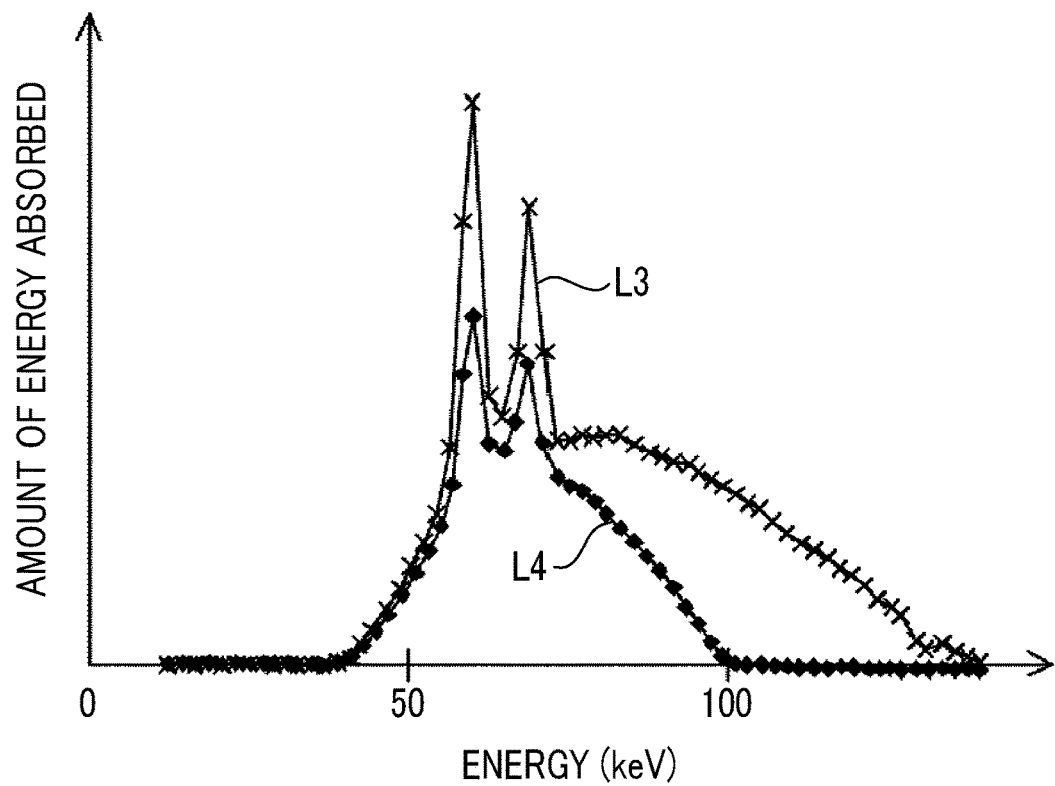
FIG. 17 is a graph illustrating the amount of radiation absorbed by a radiation detector in a case in which radiation is emitted at different tube voltages.

The radiography system 10 according to this embodiment performs two radiography operations with different tube voltages and derives bone density, using radiographic image data items obtained from the radiation detector 20C by two imaging operations. Since the tube voltages are different in the two imaging operations, the radiation detector 20C is irradiated with the radiations R with different energy levels. The radiation R absorbed by the radiation detector 20C will be described with reference to FIG. 17. In FIG. 17, the vertical axis indicates the amount of radiation R absorbed and the horizontal axis indicates the energy of the radiation R. In addition, in FIG. 17, a solid line L3 indicates the relationship between the energy of the radiation R absorbed by the radiation detector 20C and the amount of radiation R absorbed in a case in which the tube voltage of the radiation source 14 is 140 kV. In FIG. 17, a solid line L4 indicates the relationship between the energy of the radiation R absorbed by the radiation detector 20C and the amount of radiation R absorbed in a case in which the tube voltage of the radiation source 14 is 100 kV. As illustrated in FIG. 17, since the tube voltage of the radiation source 14 is different, the radiation detector 20C is irradiated with the radiations R with different energy levels in first irradiation and second irradiation.

Scattered ray correction data 95 according to this embodiment is stored in the storage unit 86 so as to be associated with a plurality of imaging conditions having at least different tube voltages. In other words, the scattered ray correction data 95 is stored in the storage unit 86 so as to be associated with a plurality of different energy levels corresponding to the tube voltages. In addition, the scattered ray correction data 95 according to this embodiment is obtained by the same calibration as that in the first embodiment.

Figure 18:
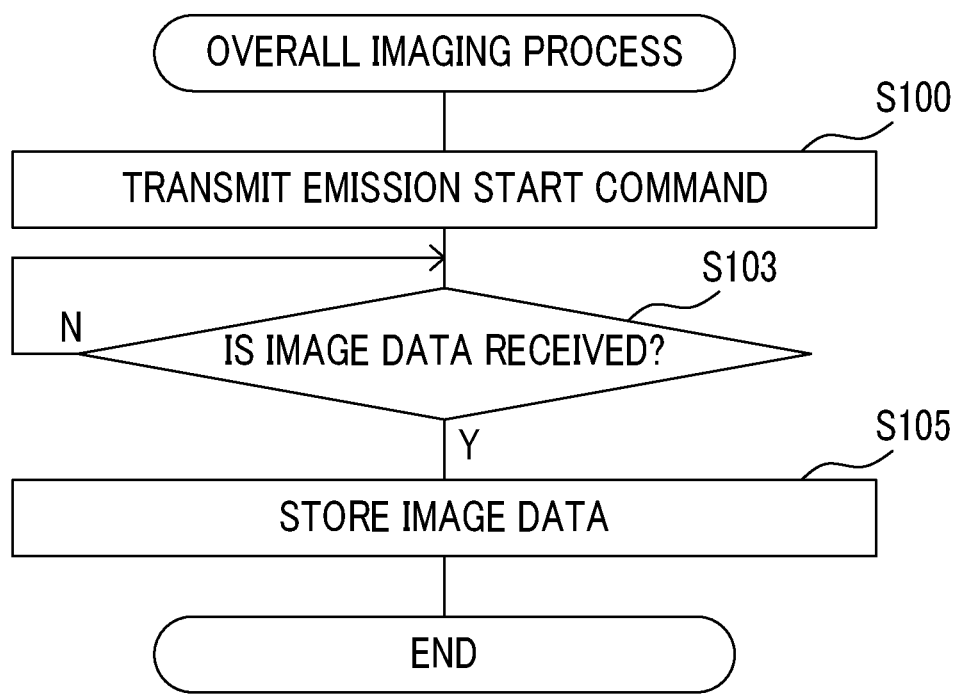
FIG. 18 is a flowchart illustrating an example of an overall imaging process according to the second embodiment.
Figure 19:
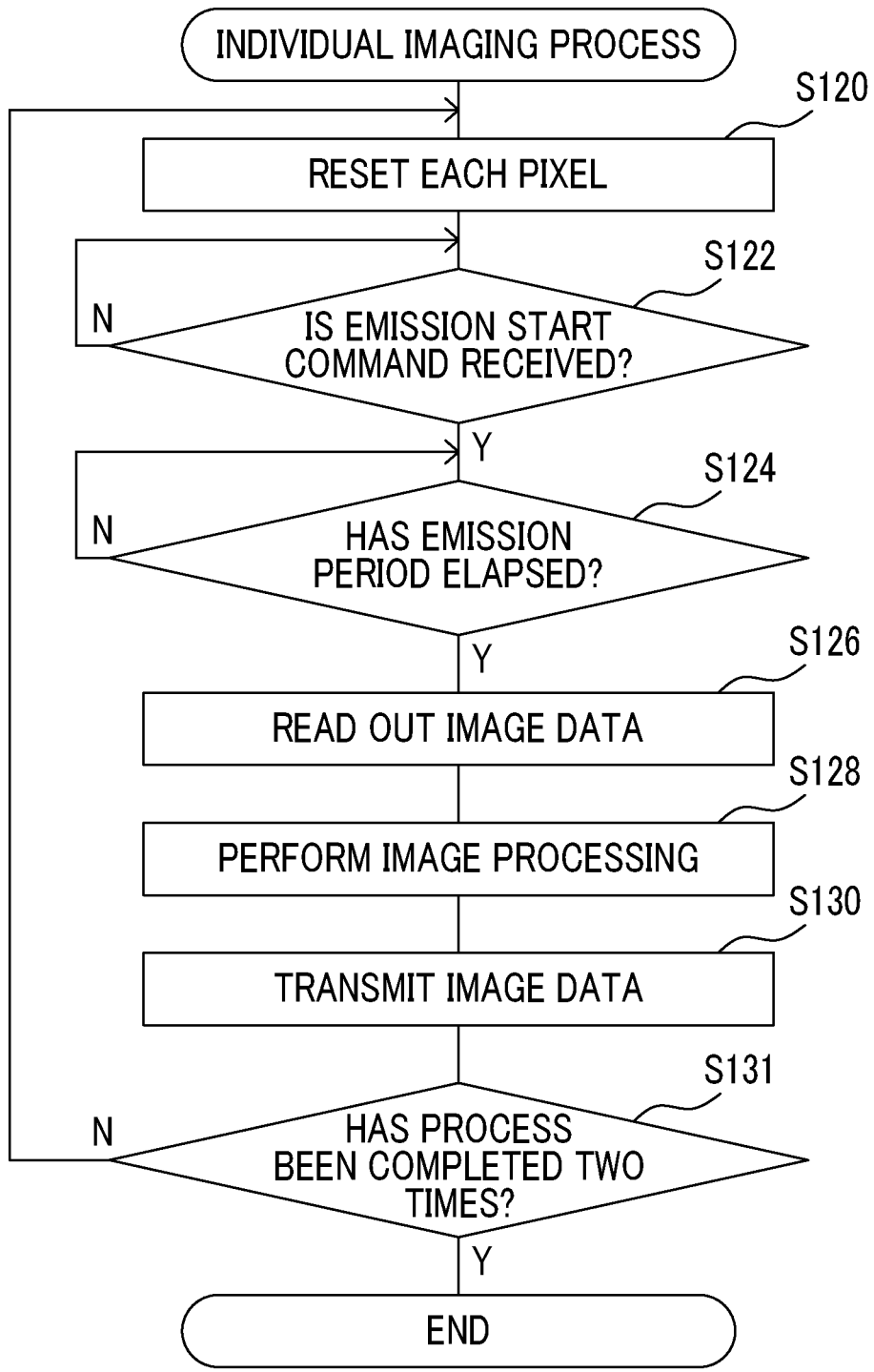
FIG. 19 is a flowchart illustrating an example of an individual imaging process according to the second embodiment.
Figure 20:
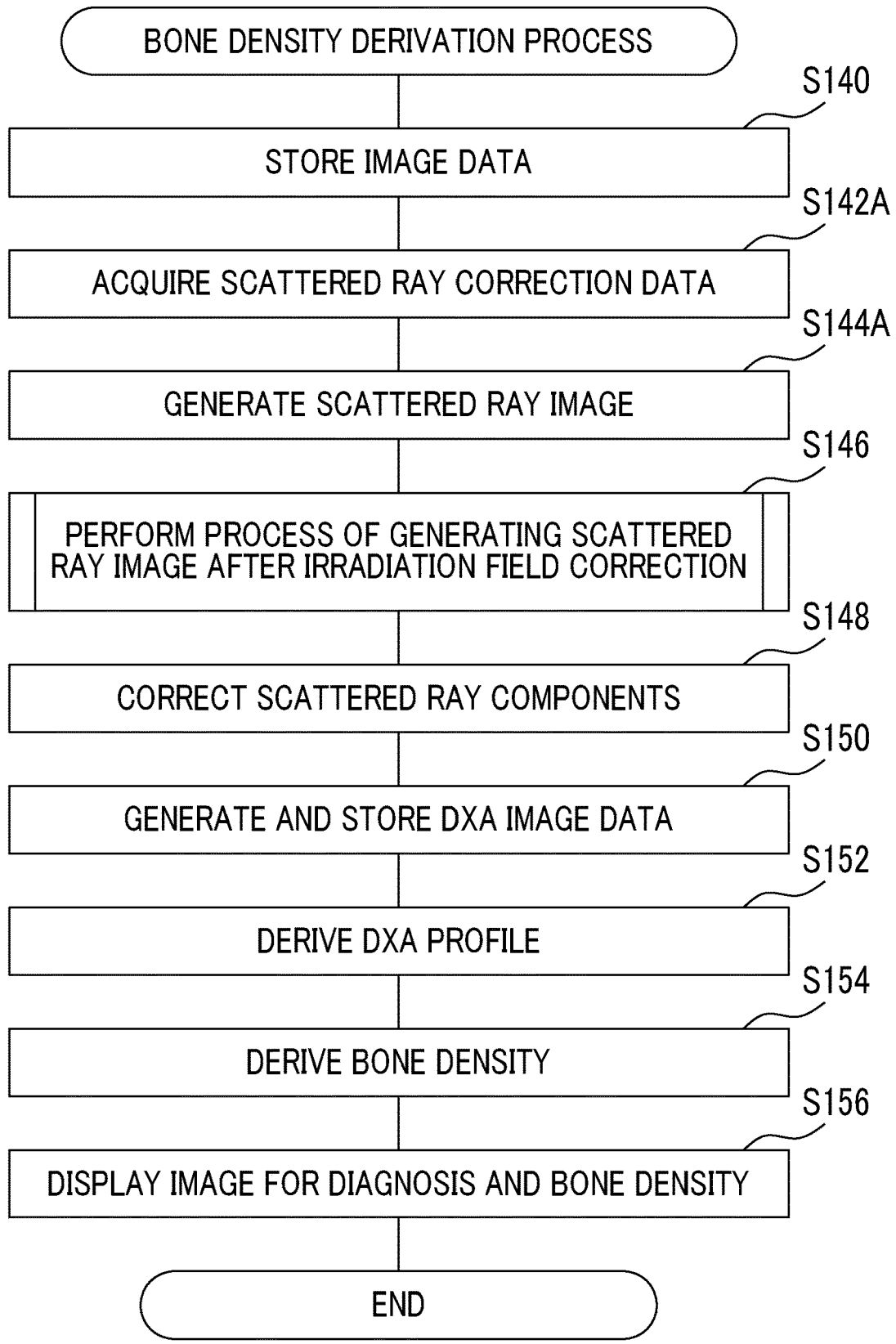
FIG. 20 is a flowchart illustrating an example of a bone density derivation process according to the second embodiment.

Next, the operation of the radiography system 10 according to this embodiment will be described with reference to FIGS. 18 to 20. In FIG. 18, steps in which the same processes as those in FIG. 10 are performed are denoted by the same reference numerals as those in FIG. 10 and the description thereof will not be repeated. In FIG. 19, steps in which the same processes as those in FIG. 11 are performed are denoted by the same reference numerals as those in FIG. 11 and the description thereof will not be repeated. In FIG. 20, steps in which the same processes as those in FIG. 12 are performed are denoted by the same reference numerals as those in FIG. 12 and the description thereof will not be repeated.

In Step S103 of FIG. 18, the CPU 80 waits until radiographic image data captured by the radiation detector 20C is received. In a case in which the CPU 80 receives radiographic image data through the communication unit 92, the determination result in Step S103 is "Yes" and the process proceeds to Step S105. In Step S105, the CPU 80 stores the radiographic image data received in Step S103 in the storage unit 86 and then ends the overall imaging process.

In this embodiment, the user performs the overall imaging process two times in a series of radiography processes. In this case, the user sets the tube voltage so as to be different in a first imaging operation and a second imaging operation. In this embodiment, a case in which the tube voltage (for example, 70 [kV]) in the first imaging operation is lower than the tube voltage in the second imaging operation and the tube voltage (for example, 100 [kV]) in the second imaging operation is higher than the tube voltage in the first imaging operation will be described. In addition, the tube voltage in the first imaging operation may be higher than the tube voltage in the second imaging operation.

In Step S131 of the individual imaging process illustrated in FIG. 19, the control unit 58A determines whether the process from Step S120 to Step S130 has been repeatedly performed two times. In a case in which the determination result in Step S131 is "No", the process returns to Step S120. On the other hand, in a case in which the determination result is "Yes", the individual imaging process ends.

The CPU 80 of the console 18 performs the following process, using the radiographic image data transmitted from the radiography apparatus 16 by the first process in Step S130 as the second radiographic image data. That is, in this case, the CPU 80 performs a bone density derivation process illustrated in FIG. 20, using the radiographic image data transmitted from the radiography apparatus 16 by the second process in Step S130 as the first radiographic image data.

In Step S142A of FIG. 20, the CPU 80 acquires the scattered ray correction data 95 associated with the imaging conditions of the first imaging operation from the storage unit 86. In addition, the CPU 80 acquires the scattered ray correction data 95 associated with the imaging conditions of the second imaging operation from the storage unit 86.

Then, in Step S144A, for the first radiographic image, the CPU 80 generates image data indicating a scattered ray image, using the scattered ray correction data 95 associated with the imaging conditions of the second imaging operation. Specifically, the CPU 80 derives the amount and spread of scattered rays for each pixel of the first radiographic image, using the scattered ray correction data 95, and performs a convolution operation for the derived amount and spread of scattered rays to generate image data indicating a scattered ray image.

In addition, for the second radiographic image, similarly, the CPU 80 generates image data indicating a scattered ray image, using the scattered ray correction data 95 associated with the imaging conditions of the first imaging operation.

In this embodiment, the same radiography apparatus 16 as that according to the first embodiment may be used. In this case, for example, a DXA image is generated from each of the radiographic images generated by irradiating the first radiation detector 20A provided on the incident side of the radiation R with the radiations R with different energy levels.

As described above, in the console 18 according to each of the above-described embodiments, the CPU 80 functions as an acquisition unit and a correction unit. The acquisition unit acquires the radiographic images (the first radiographic image and the second radiographic image) generated by the radiation detectors (20A, 20B, and 20C) irradiated with the radiation R from the radiography apparatus 16. The radiography apparatus 16 includes the radiation detectors (20A, 20B, and 20C) in which a plurality of pixels 32, each of which includes the sensor unit 32A that generates a larger amount of charge as it is irradiated with a larger amount of radiation R, are arranged. The correction unit corrects scattered ray components caused by the scattered rays of the radiation R included in the radiographic images (the first radiographic image and the second radiographic image), on the basis of subject region information indicating the regions of the radiation detectors (20A, 20B, and 20C) irradiated with the radiation R transmitted through the subject W, using the scattered ray correction data 95.

Therefore, according to the console 18 of each of the above-described embodiments, it is possible to correct components caused by the scattered rays of the radiation R included in the radiographic image with high accuracy.

In addition, for the scattered rays, the scattered ray correction data 95 (PSF 95A and intensity information 95B) varies depending on the medium of the subject (subject W). As described above, the scattered ray correction data 95 is obtained using the phantom PH. However, the phantom may be different from the actual human body. Therefore, it is preferable that calibration is performed for each part of the human body (for each part irradiated with the radiation R as the subject) in a known environment in advance, calibration data obtained by the calibration is stored so as to be associated with an imaging part, each of the PSF 95A and the intensity information 95B is corrected from the ratio to the scattered ray correction data 95, and the temporary scattered ray image or the scattered ray image after irradiation field correction is generated using the corrected PSF 95A and the corrected intensity information 95B.

Furthermore, according to this embodiment, the bone density of the subject W is derived using the radiographic images generated by each of two radiation detectors 20 provided in the radiography apparatus 16. Therefore, the bone density of the subject W can be derived by one operation of emitting the radiation R. As a result, the amount of radiation R emitted to the subject W is reduced and it is possible to derive the bone density of the subject W.

In each of the above-described embodiments, the case in which log conversion is performed for each of the values of the corresponding pixels of the first radiographic image data and the second radiographic image data and the difference between the pixel values is calculated to derive the ratio of the values of the pixels has been described. However, the invention is not limited thereto. For example, each of the values of the corresponding pixels of the first radiographic image data and the second radiographic image data may be multiplied by a weighting coefficient, log conversion may be performed for each pixel value, and the difference between the pixel values may be calculated to derive the ratio of the values of the pixels. In this case, the weighting coefficient may be a value that is obtained in advance as a coefficient for accurately deriving bone density by, for example, experiments using the actual radiography apparatus 16. For example, in a case in which the imaging part includes a region (for example, a region corresponding to the intestinal canal) including gas, such as the abdomen, a weighting coefficient for removing the pixel value of the region including gas may be used.

In each of the above-described embodiments, the bone density derivation process performed by the console 18 may be performed by the control unit 58A or the control unit 58B of the radiography apparatus 16. In addition, in a case in which the radiography apparatus 16 includes an overall control unit that controls the overall operation of the control unit 58A and the control unit 58B, the overall control unit may perform the bone density derivation process. Furthermore, for example, an information processing apparatus that is connected to the console 18 through the network may perform the bone density derivation process.

In the first embodiment, the case in which an indirect-conversion-type radiation detector that converts radiation into light and converts the converted light into charge is applied to both the first radiation detector 20A and the second radiation detector 20B has been described. However, the invention is not limited thereto. For example, a direct-conversion-type radiation detector that directly converts radiation into charge may be applied to at least one of the first radiation detector 20A or the second radiation detector 20B. In addition, for example, a conversion layer that absorbs radiation and converts the radiation into charge in the direct-conversion-type radiation detector is made of amorphous selenium (a-Se) and crystalline cadmium telluride (CdTe).

In the first embodiment, the case in which the ISS radiation detectors in which the radiation R is incident from the TFT substrates 30A and 30B are applied to the first radiation detector 20A and the second radiation detector 20B, respectively, has been described. However, the invention is not limited thereto. For example, a penetration side sampling (PSS) radiation detector in which the radiation R is incident from the scintillator 22A or 22B may be applied to at least one of the first radiation detector 20A or the second radiation detector 20B.

In each of the above-described embodiments, the case in which bone density is derived using the first radiographic image data and the second radiographic image data has been described. However, the invention is not limited thereto. For example, bone mineral content or both bone density and bone mineral content may be derived using the first radiographic image data and the second radiographic image data.

In each of the above-described embodiments, various processes performed by the execution of software (program) by the CPU may be performed by various processors other than the CPU. In this case, examples of the processor include a programmable logic device (PLD) whose circuit configuration can be changed after manufacture, such as a field-programmable gate array (FPGA), and a dedicated electric circuit, such as an application specific integrated circuit (ASIC), which is a processor having a dedicated circuit configuration designed to perform a specific process. In addition, the various processes may be performed by one of the various processors or may be performed by a combination of two or more processors of the same type or different types (for example, a combination of a plurality of FPGAs and a combination of a CPU and an FPGA). Specifically, the hardware structure of the various processors is an electric circuit obtained by combining circuit elements such as semiconductor elements.

In each of the above-described embodiments, the aspect in which the overall imaging processing program is stored (installed) in the storage unit 86 in advance has been described. However, the invention is not limited thereto. The overall imaging processing program may be recorded on a recording medium, such as a compact disk read only memory (CD-ROM), a digital versatile disk read only memory (DVD-ROM), or a universal serial bus (USB) memory, and then provided. In addition, the overall imaging processing program may be downloaded from an external apparatus through the network.

In each of the above-described embodiments, the aspect in which the individual imaging processing program is stored in the ROM of the memory 62 in the control unit 58A (control unit 58B) in advance has been described. However, the invention is not limited thereto. The individual imaging processing program may be recorded on the recording medium and then provided. In addition, the individual imaging processing program may be downloaded from an external apparatus through the network.

What is claimed is:

1. An image processing apparatus comprising:
   an acquisition unit that acquires a radiographic image generated by a radiation detector irradiated with radiation from a radiography apparatus including the radiation detector in which a plurality of pixels, each of which includes a conversion element that generates a larger amount of charge as it is irradiation with a larger amount of radiation, are arranged,
   a storage unit that stores in advance scattered ray correction data; and
   a correction unit that corrects scattered ray components caused by scattered rays of the radiation included in the radiographic image on the basis of region information indicating a region of a subject irradiated with radiation in an entire region of the radiographic image, by;
      acquiring from the storage medium scattered ray correction data associated with imaging conditions in which the radiographic image is acquired,
      using the acquired scattered ray correction data to generate a temporary scattered ray image,
      obtaining the region information by binarizing pixel values of the radiographic image,
      generating a radiographic image after irradiation field correction, for the radiographic image, using the temporary scattered ray image based on the region information.
      generating a scattered ray image after irradiation field correction using the scattered ray correction data with respect to the radiographic image after irradiation field correction, and
      correcting the scattered ray components of the radiographic image using the scattered ray image after irradiation field correction, in combination with the other claimed elements.

2. The image processing apparatus according to claim I, wherein the correction unit corrects the scattered my components, using scattered ray correction data corrected on the basis of the region information.

3. The image processing apparatus according to claim 1, wherein the scattered ray correction data includes information indicating intensity of the scattered rays and information indicating a spread of the scattered rays.

4. The image processing apparatus according to claim 1, wherein the radiography apparatus includes two radiation detectors, that is, a first radiation detector and a second radiation detector,
   the first radiation detector and the second radiation detector are arranged in a direction in which the radiation is emitted,
   the acquisition unit acquires a first radiographic image generated by the first radiation detector irradiated with radiation with a first energy level and a second radiographic image generated by the second radiation detector irradiated with radiation with a second energy level different from the first energy level, and
   the correction unit corrects the scattered ray components included in the first radiographic image, using first correction data for correcting the scattered rays which is associated with the region information and the first radiation detector, and corrects the scattered ray components included in the second radiographic image, using second correction data for correcting the scattered rays which is associated with the region information and the second radiation detector and is different from the first correction data for correcting the scattered rays.

5. The image processing apparatus according to claim 4, further comprising:
   a derivation unit that derives at least one of bone density or bone mineral content, using the first radiographic image and the second radiographic image corrected by the correction unit.

6. The image processing apparatus according to claim 4, wherein each of the first and second radiation detectors comprises a light emitting layer that is irradiated with the radiation and emits light,
   the plurality of pixels of each of the first and second radiation detectors receive the light, generate charge, and accumulate the charge, and
   the light emitting layer of one of the first and second radiation detectors which is provided on an incident side of the radiation includes CsI and the light emitting layer of the other radiation detector includes GOS.

7. The image processing apparatus according to claim 1, wherein the acquisition unit acquires a first radiographic image generated by the radiation detector irradiated with radiation with a first energy level and a second radiographic image generated by the radiation detector irradiated with radiation with a second energy level different from the first energy level, and
   the correction unit corrects the scattered ray components included in the first radiographic image, using first correction data for correcting the scattered rays which is associated with the region information and the first energy level, and corrects the scattered ray components included in the second radiographic image, using second correction data for correcting the scattered rays which is associated with the region information and the second energy level and is different from the first correction data for correcting the scattered rays.

8. The image processing apparatus according to claim 7, further comprising:
   a derivation unit that derives at least one of bone density or bone mineral content, using the first radiographic image and the second radiographic image corrected by the correction unit.

9. A radiography system comprising:
the image processing apparatus according to claim 1; and
a radiography apparatus that outputs a radiographic image to the image processing apparatus.

10. An image processing method comprising:
storing in advance scattered ray correction data;
acquiring a radiographic image generated by a radiation detector irradiated with radiation from a radiography apparatus including the radiation detector in which a plurality of pixels, each of which includes a conversion element that generates a larger amount of charge as it is irradiated with a larger amount of radiation, are arranged; and
correcting scattered ray components caused by scattered rays of the radiation included in the radiographic image on the basis of region information indicating a region of a subject irradiated with radiation in an entire region of the radiographic image, by:
acquiring from the storage medium scattered ray correction data associated with imaging conditions in which the radiographic image is acquired,
using the acquired scattered ray correction data to generate a temporary scattered ray image,
obtaining the region information by binarizing pixel values of the radiographic image,
generating a radiographic image after irradiation field correction, for the radiographic image, using the temporary scattered ray image based on the region information,
generating a scattered ray image after irradiation field correction using the scattered ray correction data with respect to the radiographic image after irradiation field correction, and
correcting the scattered ray components of the radiographic image using the scattered ray image after irradiation field correction.

11. A non-transitory storage medium storing a program that causes a computer to perform an image processing, the image processing comprising:
storing in advance scattered ray correction data;
acquiring a radiographic image generated by a radiation detector irradiated with radiation from a radiography apparatus including the radiation detector in which a plurality of pixels, each of which includes a conversion element that generates a larger amount of charge as it is irradiated with a larger amount of radiation, are arranged; and
correcting scattered ray components caused by scattered rays of the radiation included in the radiographic image on the basis of region information indicating a region of a subject irradiated with radiation in an entire region of the radiographic image, by:
acquiring from the storage medium scattered ray correction data associated with imaging conditions in which the radiographic image is acquired,
using the acquired scattered ray correction data to generate a temporary scattered ray image,
obtaining the region information by binarizing pixel values of the radiographic image,
generating a radiographic image after irradiation field correction for the radiographic image. using the temporary scattered ray image based on the region information,
generating a scattered ray image after irradiation field correction using the scattered ray correction data with respect to the radiographic image after irradiation field correction, and
correcting the scattered ray components of the radiographic image using the scattered ray image after irradiation field correction.

* * * * *